(12) United States Patent
Takeuchi et al.

(10) Patent No.: US 7,271,147 B2
(45) Date of Patent: Sep. 18, 2007

(54) ANTIBIOTICS, TRIPROPEPTINS AND PROCESS FOR PRODUCING THE SAME

(75) Inventors: Tomio Takeuchi, Tokyo (JP); Hideki Hashizume, Tokyo (JP); Masayuki Igarashi, Atsugi (JP); Hiroshi Naganawa, Tokyo (JP); Masa Hamada, Tokyo (JP)

(73) Assignee: Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 580 days.

(21) Appl. No.: 10/239,324

(22) PCT Filed: Mar. 28, 2001

(86) PCT No.: PCT/JP01/02578

§ 371 (c)(1),
(2), (4) Date: Nov. 7, 2002

(87) PCT Pub. No.: WO01/74850

PCT Pub. Date: Oct. 11, 2001

(65) Prior Publication Data

US 2003/0162697 A1    Aug. 28, 2003

(30) Foreign Application Priority Data

Mar. 30, 2000    (JP) .............................. 2000-093405

(51) Int. Cl.
*A01K 31/16*    (2006.01)
*C12P 21/06*    (2006.01)
*C12N 1/20*    (2006.01)

(52) U.S. Cl. ........................ 514/9; 435/68.1; 435/252.1

(58) Field of Classification Search ................ 435/68.1, 435/252.1; 514/9
See application file for complete search history.

(56) References Cited

U.S. PATENT DOCUMENTS 4,754,018 A * 6/1988 Tymiak et al. .............. 530/317

\* cited by examiner

*Primary Examiner*—Leon B. Lankford, Jr.
*Assistant Examiner*—Susan Hanley
(74) *Attorney, Agent, or Firm*—Abelman, Frayne & Schwab

(57) ABSTRACT

By culturing *Lysobacter* sp. BMK333-48F3 (deposit number of FERM BP-7477), an antibiotic, tripropeptin Z, tripropeptin A, tripropeptin B, tripropeptin C or tripropeptin D represented by the general formula (I):

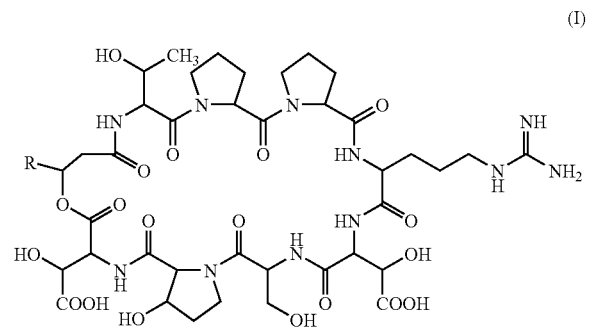

wherein R is 7-methyl-octyl group, 8-methyl-nonyl group, 9-methyl-dodecyl group, 10-methyl-undecyl group or 11-methyl-dodecyl group, is obtained as antibiotics having excellent antibacterial activities against bacteria and having a novel molecular structure. These tripropeptins each have an excellent antibacterial activity against various bacteria and drug-resistant strains thereof, such as methicillin-resistant strains and vancomycin-resistant strains.

10 Claims, 15 Drawing Sheets

ANTIBIOTICS, TRIPROPEPTINS AND PROCESS FOR PRODUCING THE SAME

TECHNICAL FIELD

This application is a 371 of PCT/JP01/02578, filed Mar. 28, 2001 which claims foreign priority under 35 U.S.C. 119(a-d) from JP 2000-93405, filed Mar. 30, 2000.

This invention relates to new antibiotics, namely tripropeptins Z, A, B, C and D or pharmaceutically acceptable salts thereof, which each have excellent antibacterial activities. This invention also relates to a process for producing a tripropeptin. Further, this invention relates to a pharmaceutical composition, particularly an antibacterial composition, comprising a tripropeptin or a pharmaceutically acceptable salt thereof as an active ingredient. Still further, this invention relates to Lysobacter sp. BMK333-48F3, as a new microorganism, having a characteristic nature that it is capable of producing a tripropeptin.

BACKGROUND ART

As antibiotics were commonly used, multi-drug-resistant bacteria, particularly methicillin-resistant bacteria have widely occurred and these resistant bacteria have brought about a clinical problem. The methicillin-resistant bacteria can exhibit a resistance not only against methicillin but also against many antibiotics such as antibiotics of aminoglycosides, tetracyclines, β-lactams and macrolides.

In recent years, drug-resistant bacteria have appeared even against vancomycin which is an antibiotic known as a last remaining card for the therapy of infections of the methicillin-resistant bacteria. Thus, there is now a keen request for finding and providing a novel compound which can exhibit excellent antibacterial activities against the drug-resistant bacteria, particularly the methicillin-resistant bacteria and vancomycin-resistant bacteria.

An object of this invention is to provide a novel antibiotic which has excellent antibacterial activities and is capable of meeting the requisites as above-mentioned.

DISCLOSURE OF THE INVENTION

We, the inventors of this invention, have carried out our investigations with the intention of finding out useful antibiotics. As a result, we have early found that a new bacterial strain, Lysobacter sp. BMK333-48F3, which belongs to the genus Lysobacter and which has been isolated from a soil sample by us, can produce a novel antibiotic having high antibacterial activities against gram-positive bacteria and their drug-resistant bacteria. We have designated this novel antibiotic as tripropeptin. Although this tripropeptin is in the form of colorless powders of which chemical structure has not been determined, tripropeptin has been isolated as a substance having a molecular formula of $C_{51}H_{83}N_{11}O_{19}$ (Japanese patent application 2000-93405 filed on Mar. 30, 2000). We have further proceeded with our studies and have now found that, in addition to the above-mentioned tripropeptin, said strain Lysobacter sp. BMK333-48F3 produces further four antibiotics. We have now designated these five antibiotics, including tripropeptin and the latter four antibiotics, collectively, as a tripropeptin. We have now further found that a tripropeptin exhibits high antibacterial activities against gram-positive bacteria and their drug-resistant bacteria. We have further proceeded with our studies and have now confirmed from the Physico-chemical analysis of tripropeptins that there are five compounds which are embraced by a class of tripropeptins. As a result, we have re-named the tripropeptin previously obtained, into tripropeptin C and also have designated the latter four compounds now obtained, as tripropeptins Z, A, B and D, respectively. We have now determined chemical structures of these five compounds. Furthermore, we have now confirmed and found that tripropeptins Z, A, B, C and D are novel compounds and they are collectively represented by a general formula (I) given below. Further, it is revealed that these tripropeptins have a common and basic skeletal structure as shown in the general formula (I), wherein the side chain group R denotes branched alkyl groups of 8 to 12 carbon atoms different from each other.

According to a first aspect of this invention, therefore, there is provided an antibiotic, tripropeptin Z, tripropeptin A, tripropeptin B, tripropeptin C or tripropeptin D, which is a compound represented by the following general formula (I)

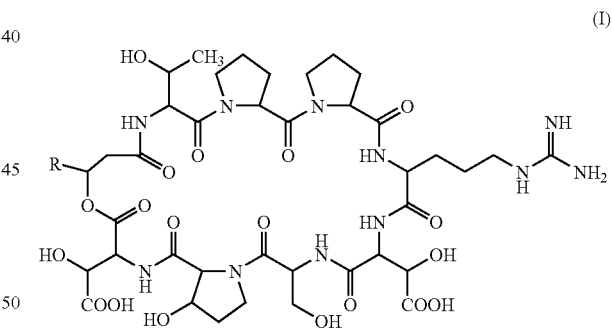

wherein R is 7-methyl-octyl group for tripropeptin Z; 8-methyl-nonyl group for tripropeptin A; 9-methyl-dodecyl group for tripropeptin B; 10-methyl-undecyl group for tripropeptin C; and 11-methyl-dodecyl group for tripropeptin D, or a pharmaceutically acceptable salt thereof.

A tripropeptin of the general formula (I) according to the first aspect of this invention embraces tripropeptin Z of formula (Iz), tripropeptin A of formula (Ia), tripropeptin B of formula (Ib), tripropeptin C of formula (Ic) and tripropeptin D of formula (Id) as shown below:

(1) Tripropeptin Z represented by the formula (Iz):
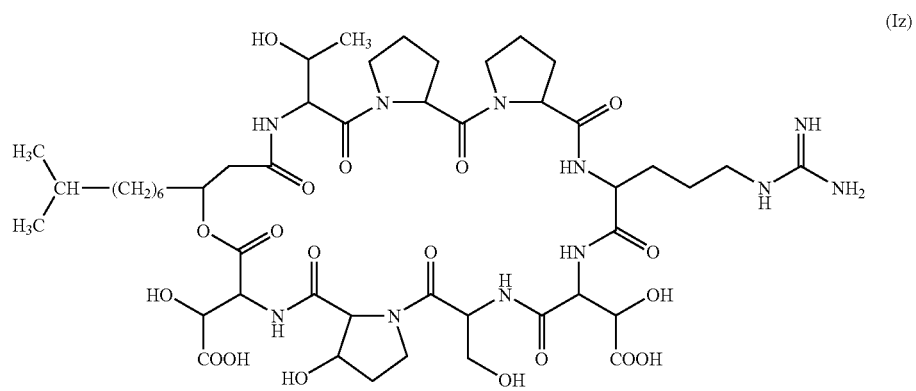
[Compound of the general formula (I) where R is 7-methyl-octyl group];
(2) Tripropeptin A represented by the formula (Ia):
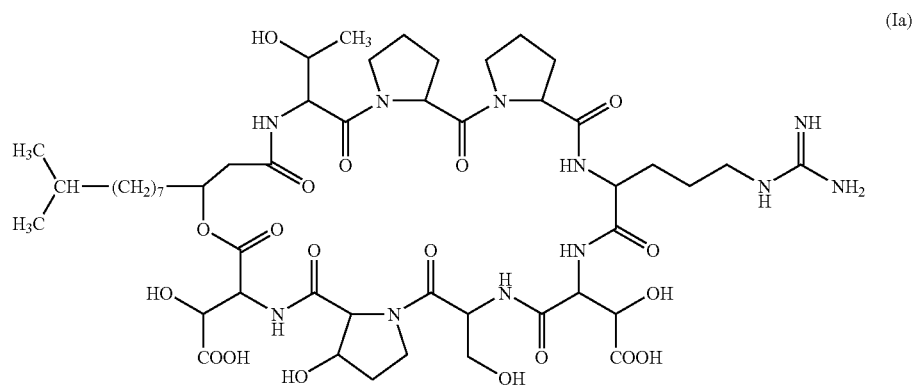
[Compound of the general formula (I) where R is 8-methyl-nonyl group];
(3) Tripropeptin B represented by the formula (Ib):
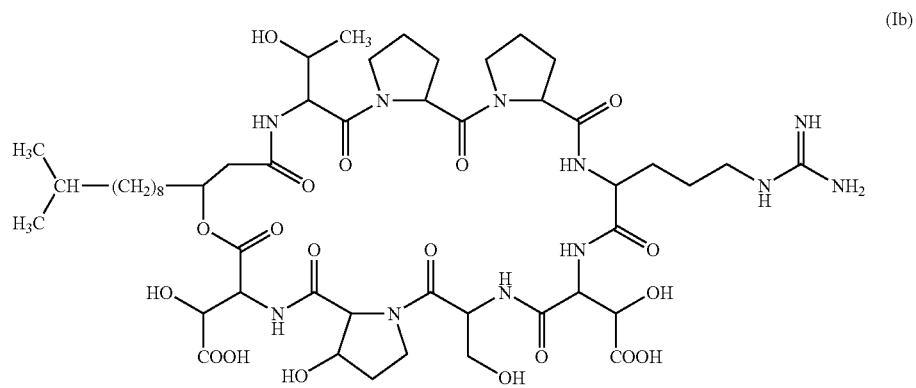
[Compound of the general formula (I) where R is 9-methyl-decyl group];

(4) Tripropeptin C represented by the formula (Ic):

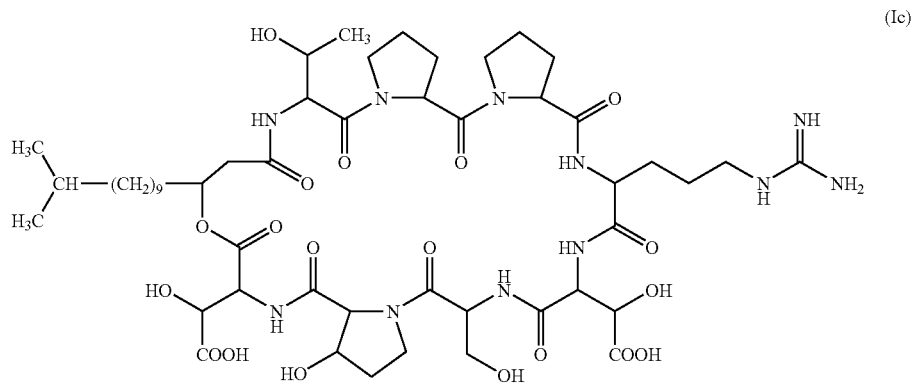

[Compound of the general formula (I) where R is 10-methyl-undecyl group]; and (5) Tripropeptin D represented by the formula (Id):

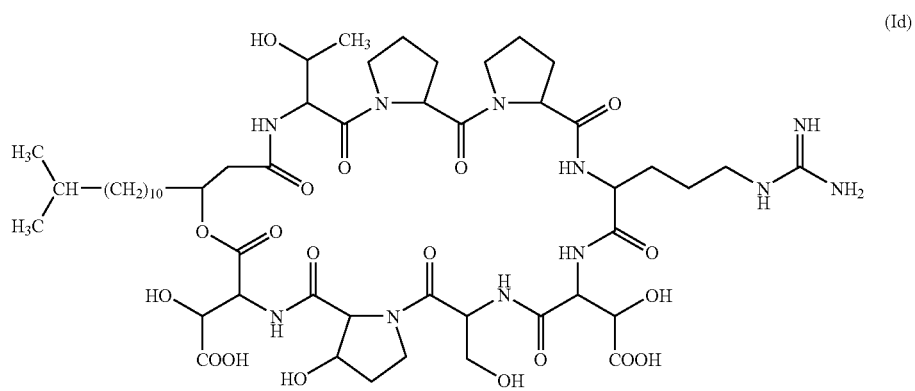

[Compound of the general formula (I) where R is 11-methyl-dodecyl group].

Physico-chemical properties of tripropeptin Z of the formula (Iz) according to the first aspect of this invention are as follows.

(1) Appearance
Colorless powder (2) Molecular formula
$C_{48}H_{77}N_{11}O_{19}$ (3) High resolution mass spectrometry (HRFABMS: cation mode)

| Found: | 1112.5475 $(M + H)^+$ |
| Calculated: | 1112.5490 |

(4) Specific rotation
$[\alpha]_D^{24}$ −14.0° (c 1, $CH_3OH$)

(5) Ultraviolet absorption spectrum (in methanol)
$\lambda_{max}$ nm ($\epsilon$): End absorption (6) Infrared absorption spectrum
As shown in FIG. 1 of attached drawings.

(7) Proton nuclear magnetic resonance spectrum
Proton NMR spectrum as measured in DMSO-$d_6$-$D_2O$ (20:1) at 500 MHz at room temperature is shown in FIG. 2 of attached drawings.

(8) $^{13}C$-nuclear magnetic resonance spectrum
$^{13}C$-NMR spectrum as measured in DMSO-$d_6$-$D_2O$ (20:1) at 125 MHz at room temperature is shown in FIG. 3 of attached drawings.

(9) Solubility
Soluble in methanol, dimethyl sulfoxide (DMSO) and water, but insoluble in acetone, ethyl acetate and chloroform.

(10) TLC
When it is subjected to a thin layer chromatography on silica gel 60$F_{254}$ (a product of Merck & Co.) as developed with a solvent consisting of butanol-methanol-water (4:1:2), the $R_f$ value is 0.25.

Tripropeptin Z according to the first aspect of this invention is an amphoteric substance, and the pharmaceutically acceptable salts thereof may be exemplified by its salts with organic bases such as quaternary ammonium salts, its salts with various metals, for example, its salts with alkali metals such as sodium salt, or its acid addition salts with organic acids such as acetic acid or with inorganic acid such as hydrochloric acid.

Physico-chemical properties of tripropeptin A of the formula (Ia) according to the first aspect of this invention are as follows.

(1) Appearance
Colorless powder (2) Molecular formula
$C_{49}H_{79}N_{11}O_{19}$ (3) High resolution mass spectrometry (HRFABMS: cation mode)

| Found: | 1126.5632 $(M + H)^+$ |
|---|---|
| Calculated: | 1126.5657 |

(4) Specific rotation
$[\alpha]_D^{24}$ −7.8° (c 1, $CH_3OH$)

(5) Ultraviolet absorption spectrum (in methanol)
$\lambda_{max}$ nm ($\epsilon$): End absorption (6) Infrared absorption spectrum
As shown in FIG. 4 of attached drawings.

(7) Proton nuclear magnetic resonance spectrum
Proton NMR spectrum as measured in a solvent mixture of DMSO-$d_6$-$D_2O$ (20:1) at 500 MHz at room temperature is shown in FIG. 5 of attached drawings.

(8) $^{13}C$-nuclear magnetic resonance spectrum
$^{13}C$-NMR spectrum as measured in a solvent mixture of DMSO-$d_6$-$D_2O$ (20:1) at 125 MHz at room temperature is shown in FIG. 6 of attached drawings.

(9) Solubility
Soluble in methanol, DMSO and water, but insoluble in acetone, ethyl acetate and chloroform.

(10) TLC
When it is subjected to a thin layer chromatography on silica gel 60$F_{254}$ (a product of Merck & Co.) as developed with a solvent consisting of butanol-methanol-water (4:1:2), the $R_f$ value is 0.25.

Tripropeptin A according to the first aspect of this invention is an amphoteric substance, and the pharmaceutically acceptable salts thereof may be exemplified by its salts with organic bases such as quaternary ammonium salts, its salts with various metals, for example, its salts with alkali metals such as sodium salt, or its acid addition salts with organic acids such as acetic acid or with inorganic acid such as hydrochloric acid.

Physico-chemical properties of tripropeptin C of the formula (Ib) according to the first aspect of this invention are as follows.

(1) Appearance
Colorless powder (2) Molecular formula
$C_{50}H_{81}N_{11}O_{19}$ (3) High resolution mass spectrometry (HRFABMS: cation mode)

| Found: | 1140.5788 $(M + H)^+$ |
|---|---|
| Calculated: | 1140.5776 |

(4) Specific rotation
$[\alpha]_D^{24}$ −7.9° (c 1, $CH_3OH$)

(5) Ultraviolet absorption spectrum (in methanol)
$\lambda_{max}$ nm ($\epsilon$): End absorption (6) Infrared absorption spectrum
As shown in FIG. 7 of attached drawings.

(7) Proton nuclear magnetic resonance spectrum
Proton NMR spectrum as measured in a solvent mixture of DMSO-$d_6$-$D_2O$ (20:1) at 125 MHz at room temperature is shown in FIG. 8 of attached drawings.

(8) $^{13}C$-nuclear magnetic resonance spectrum
$^{13}C$-NMR spectrum as measured in a solvent mixture of DMSO-$d_6$-$D_2O$ (20:1) at 125 MHz at room temperature is shown in FIG. 9 of attached drawings.

(9) Solubility
Soluble in methanol, DMSO and water, but insoluble in acetone, ethyl acetate and chloroform.

(10) TLC
When it is subjected to a thin layer chromatography on silica gel 60$F_{254}$ (a product of Merck & Co.) as developed with a solvent consisting of butanol-methanol-water (4:1:2), the $R_f$ value is 0.25.

Tripropeptin B according to the first aspect of this invention is an amphoteric substance, and the pharmaceutically acceptable salts thereof may be exemplified by its salts with organic bases such as quaternary ammonium salts, its salts with various metals, for example, its salts with alkali metals such as sodium salt, or its acid addition salts with organic acids such as acetic acid or with inorganic acid such as hydrochloric acid.

Physico-chemical properties of tripropeptin C of the formula (Ic) according to the first aspect of this invention are as follows.

(1) Appearance
Colorless powder (2) Molecular formula
$C_{51}H_{83}N_{11}O_{19}$ (3) High resolution mass spectrometry (HRFABMS: cation mode)

| Found: | 1154.5927 $(M + H)^+$ |
|---|---|
| Calculated: | 1154.5945 |

(4) Specific rotation
$[\alpha]_D^{24}$ −8.4 ° (c 1, $CH_3OH$)

(5) Ultraviolet absorption spectrum (in methanol)
$\lambda_{max}$ nm ($\epsilon$): End absorption (6) Infrared absorption spectrum
As shown in FIG. 10 of attached drawings.

(7) Proton nuclear magnetic resonance spectrum
Proton NMR spectrum as measured in a solvent mixture of DMSO-$d_6$-$D_2O$ (20:1) at 500 MHz at room temperature is shown in FIG. 11 of attached drawings.

(8) $^{13}C$-nuclear magnetic resonance spectrum
$^{13}C$-NMR spectrum as measured in a solvent mixture of DMSO-$d_6$-$D_2O$ (20:1) at 125 MHz at room temperature is shown in FIG. 12 of attached drawings.

(9) Solubility

Soluble in methanol, DMSO and water, but insoluble in acetone, ethyl acetate and chloroform.

(10) TLC

When it is subjected to a thin layer chromatography on silica gel 60F$_{254}$ (a product of Merck & Co.) as developed with a solvent consisting of butanol-methanol-water (4:1:2), the R$_f$ value is 0.25.

Tripropeptin C according to the first aspect of this invention is an amphoteric substance, and the pharmaceutically acceptable salts thereof may be exemplified by its salts with organic bases such as quaternary ammonium salts, its salts with various metals, for example, its salts with alkali metals such as sodium salt, or its acid addition salts with organic acids such as acetic acid or with inorganic acid such as hydrochloric acid.

Physico-chemical properties of tripropeptin D of the formula (Id) according to the first aspect of this invention are as follows.

(1) Appearance

Colorless powder (2) Molecular formula $C_{52}H_{85}N_{11}O_{19}$ (3) High resolution mass spectrometry (HRFABMS: cation mode)

| Found: | 1168.6101 (M + H)$^+$ |
|---|---|
| Calculated: | 1168.6074 |

(4) Specific rotation $[\alpha]_D^{24}$ –13.8° (c 1, CH$_3$OH)

(5) Ultraviolet absorption spectrum (in methanol)

$\lambda_{max}$ nm ($\epsilon$): End absorption (6) Infrared absorption spectrum As shown in FIG. 13 of attached drawings.

(7) Proton nuclear magnetic resonance spectrum

Proton NMR spectrum as measured in a solvent mixture of DMSO-d$_6$-D$_2$O (20:1) at 500 MHz at room temperature is shown in FIG. 14 of attached drawings.

(8) $^{13}$C-nuclear magnetic resonance spectrum $^{13}$C-NMR spectrum as measured in a solvent mixture of DMSO-d$_6$-D$_2$O (20:1) at 125 MHz at room temperature is shown in FIG. 15 of attached drawings.

(9) Solubility

Soluble in methanol, DMSO and water, but insoluble in acetone, ethyl acetate and chloroform.

(10) TLC

When it is subjected to a thin layer chromatography on silica gel 60F$_{254}$ (a product of Merck & Co.) as developed with a solvent consisting of butanol-methanol-water (4:1:2), the R$_f$ value is 0.25.

Tripropeptin D according to the first aspect of this invention is an amphoteric substance, and the pharmaceutically acceptable salts thereof may be exemplified by its salts with organic bases such as quaternary ammonium salts, its salts with various metals, for example, its salts with alkali metals such as sodium salt, or its acid addition salts with organic acids such as acetic acid or with inorganic acid such as hydrochloric acid.

By the way, the expression "a tripropeptin" simply given in this description may sometime mean either any one of tripropeptin Z, tripropeptin A, tripropeptin B, tripropeptin C and tripropeptin D, or a mixture of two or more or a mixture of all of them.

Tripropeptins having the general formula (I) above according to this invention have biological properties hereinafter given.

Thus, tripropeptin Z, tripropeptin A, tripropeptin B, tripropeptin C and tripropeptin D each exhibit antibacterial activities against gram-positive bacteria, including drug-resistant strains (methicillin-resistant strains, and others). The antibacterial activities of a tripropeptin against these bacteria are tested by the following procedures.

TEST EXAMPLE 1

Minimum growth inhibitory concentrations (µg/ml) of tripropeptin Z against a variety of microorganisms were measured on a Mueller-Hinton agar medium (manufactured by Difco Laboratories) or on a 5% sheep blood-supplemented Mueller-Hinton agar medium (manufactured by Difco Laboratories) for *Enterococcus*, by a serial dilution method according to the standard method as provided by Japanese Society of Chemotherapy. The resulting antibacterial spectra are shown in Table 1.

TABLE 1

| Microorganisms tested | Tripropeptin Z Minimum growth inhibitory concentration (µg/ml) |
|---|---|
| *Staphylococcus aureus* FDA209P | 12.5 |
| *Staphylococcus aureus* Smith | 6.25 |
| *Staphylococcus aureus* MS9610 (multi-drug-resistant) | 25 |
| *Staphylococcus aureus* MS16460 (methicillin-resistant) | 50 |
| *Staphylococcus aureus* MS16497 (methicillin-resistant) | 25 |
| *Staphylococcus aureus* MS16526 (methicillin-resistant) | 25 |
| *Staphylococcus aureus* TY-00933 (methicillin-resistant) | 25 |
| *Staphylococcus aureus* TY-03454 (methicillin-resistant) | 25 |
| *Staphylococcus aureus* TY-03456 (methicillin-resistant) | 25 |
| *Staphylococcus aureus* TY-04282 (methicillin-resistant) | 25 |
| *Micrococcus luteus* FDA16 | <0.39 |
| *Bacillus anthracis* | 100 |
| *Bacillus subtilis* PCI219 | 25 |
| *Bacillus cereus* ATCC10702 | >50 |
| *Corynebacterium bovis* 1810 | 6.25 |
| *Shigella sonnei* JS11746 | >100 |
| *Salmonella typhi* T-63 | >50 |
| *Kiebsiella pneumoniae* PCI602 | >50 |
| *Enterococcus faecalis* JCM5803 | 100 |
| *Enterococcus faecium* JCM5804 | >100 |
| *Enterococcus faecalis* NCTC 12201 (vancomycin-resistant) | 100 |
| *Enterococcus faecium* NCTC 12202 (vancomycin-resistant) | >100 |
| *Enterococcus faecalis* NCTC 12203 (vancomycin-resistant) | >100 |
| *Enterococcus faecium* NCTC 12204 (vancomycin-resistant) | >100 |

TEST EXAMPLE 2

Minimum growth inhibitory concentrations (µg/ml) of tripropeptin A against a variety of microorganisms were measured on a Mueller-Hinton agar medium (manufactured by Difco Laboratories) or on a 5% sheep blood-supplemented Mueller-Hinton agar medium (manufactured by Difco Laboratories) for *Enterococcus*, by a serial dilution method according to the standard method as provided by Japanese Society of Chemotherapy. The resulting antibacterial spectra are shown in Table 2.

TABLE 2

| Microorganisms tested | Tripropeptin A Minimum growth inhibitory concentration (µg/ml) |
|---|---|
| *Staphylococcus aureus* FDA209P | 1.56 |
| *Staphylococcus aureus* Smith | 0.78 |
| *Staphylococcus aureus* MS9610 (multi-drug-resistant) | 6.25 |
| *Staphylococcus aureus* MS16460 (methicillin-resistant) | 6.25 |
| *Staphylococcus aureus* MS16497 (methicillin-resistant) | 6.25 |
| *Staphylococcus aureus* MS16526 (methicillin-resistant) | 3.13 |
| *Staphylococcus aureus* TY-00933 (methicillin-resistant) | 6.25 |
| *Staphylococcus aureus* TY-03454 (methicillin-resistant) | 6.25 |
| *Staphylococcus aureus* TY-03456 (methicillin-resistant) | 6.25 |
| *Staphylococcus aureus* TY-04282 (methicillin-resistant) | 6.25 |
| *Micrococcus luteus* FDA16 | <0.39 |
| *Bacillus anthracis* | 25 |
| *Bacillus subtilis* PCI219 | 3.13 |
| *Bacillus cereus* ATCC10702 | 12.3 |
| *Corynebacterium bovis* 1810 | 1.56 |
| *Shigella sonnei* JS11746 | >100 |
| *Salmonella typhi* T-63 | >50 |
| *Klebsiella pneumoniae* PCI602 | >50 |
| *Enterococcus faecalis* JCM5803 | 50 |
| *Enterococcus faecium* JCM5804 | 50 |
| *Enterococcus faecalis* NCTC 12201 (vancomycin-resistant) | 50 |
| *Enterococcus faecium* NCTC 12202 (vancomycin-resistant) | 50 |
| *Enterococcus faecalis* NCTC 12203 (vancomycin-resistant) | 50 |
| *Enterococcus faecium* NCTC 12204 (vancomycin-resistant) | 50 |

TEST EXAMPLE 3

Minimum growth inhibitory concentrations (µg/ml) of tripropeptin B against a variety of microorganisms were measured on a Mueller-Hinton agar medium (manufactured by Difco Laboratories) or on a 5% sheep blood-supplemented Mueller-Hinton agar medium (manufactured by Difco Laboratories) for *Enterococcus*, by a serial dilution method according to the standard method as provided by Japanese Society of Chemotherapy. The resulting antibacterial spectra are shown in Table 3.

TABLE 3

| Microorganisms tested | Tripropeptin B Minimum growth inhibitory concentration (µg/ml) |
|---|---|
| *Staphylococcus aureus* FDA209P | 1.56 |
| *Staphylococcus aureus* Smith | 1.56 |
| *Staphylococcus aureus* MS9610 (multi-drug-resistant) | 3.13 |
| *Staphylococcus aureus* MS16460 (methicillin-resistant) | 6.25 |
| *Staphylococcus aureus* MS16497 (methicillin-resistant) | 3.13 |
| *Staphylococcus aureus* MS16526 (methicillin-resistant) | 3.13 |
| *Staphylococcus aureus* TY-00933 (methicillin-resistant) | 3.13 |
| *Staphylococcus aureus* TY-03454 (methicillin-resistant) | 3.13 |
| *Staphylococcus aureus* TY-03456 (methicillin-resistant) | 3.13 |
| *Staphylococcus aureus* TY-04282 (methicillin-resistant) | 3.13 |
| *Micrococcus luteus* FDA16 | 0.20 |
| *Bacillus anthracis* | 6.25 |
| *Bacillus subtilis* PC1219 | 1.56 |
| *Bacillus cereus* ATCC10702 | >100 |
| *Corynebacterium bovis* 1810 | 0.78 |
| *Shigella sonnei* JS11746 | >100 |
| *Salmonella typhi* T-63 | >100 |
| *Klebsiella pneumoniae* PCI602 | >100 |
| *Enterococcus faecalis* JCM5803 | 25 |
| *Enterococcus faecium* JCM5804 | 25 |
| *Enterococcus faecalis* NCTC 12201 (vancomycin-resistant) | 12.5 |
| *Enterococcus faecium* NCTC 12202 (vancomycin-resistant) | 25 |
| *Enterococcus faecalis* NCTC 12203 (vancomycin-resistant) | 50 |
| *Enterococcus faecium* NCTC 12204 (vancomycin-resistant) | 25 |

TEST EXAMPLE 4

Minimum growth inhibitory concentrations (µg/ml) of tripropeptin C against a variety of microorganisms were measured on a Mueller-Hinton agar medium (manufactured by Difco Laboratories) or on a 5% sheep blood-supplemented Mueller-Hinton agar medium (manufactured by Difco Laboratories) for *Enterococcus*, by a serial dilution method according to the standard method as provided by Japanese Society of Chemotherapy. The resulting antibacterial spectra are shown in Table 4.

TABLE 4

| Microorganisms tested | Tripropeptin C Minimum growth inhibitory concentration (µg/ml) |
|---|---|
| *Staphylococcus aureus* FDA209P | 1.56 |
| *Staphylococcus aureus* Smith | 1.56 |
| *Staphylococcus aureus* MS9610 (multi-drug-resistant) | 1.56 |
| *Staphylococcus aureus* MS16460 (methicillin-resistant) | 3.13 |
| *Staphylococcus aureus* MS16497 (methicillin-resistant) | 1.56 |
| *Staphylococcus aureus* MS16526 (methicillin-resistant) | 1.56 |

TABLE 4-continued

| Microorganisms tested | Tripropeptin C Minimum growth inhibitory concentration (µg/ml) |
|---|---|
| *Staphylococcus aureus* TY-00933 (methicillin-resistant) | 3.13 |
| *Staphylococcus aureus* TY-03454 (methicillin-resistant) | 1.56 |
| *Staphylococcus aureus* TY-03456 (methicillin-resistant) | 3.13 |
| *Staphylococcus aureus* TY-04282 (methicillin-resistant) | 1.56 |
| *Micrococcus luteus* FDA16 | 0.20 |
| *Bacillus anthracis* | 3.13 |
| *Bacillus subtilis* PCI219 | 1.56 |
| *Bacillus cereus* ATCC10702 | 3.13 |
| *Corynebacterium bovis* 1810 | 0.39 |
| *Shigella sonnei* JS11746 | >100 |
| *Salmonella typhi* T-63 | >100 |
| *Klebsiella pneumoniae* PCI602 | >100 |
| *Enterococcus faecalis* JCM5803 | 12.5 |
| *Enterococcus faecium* JCM5804 | 12.5 |
| *Enterococcus faecalis* NCTC 12201 (vancomycin-resistant) | 6.25 |
| *Enterococcus faecium* NCTC 12202 (vancomycin-resistant) | 12.5 |
| *Enterococcus faecalis* NCTC 12203 (vancomycin-resistant) | 25 |
| *Enterococcus faecium* NCTC 12204 (vancomycin-resistant) | 12.5 |

TEST EXAMPLE 5

Minimum growth inhibitory concentrations (µg/ml) of tripropeptin D against a variety of microorganisms were measured on a Mueller-Hinton agar medium (manufactured by Difco Laboratories) or on a 5% sheep blood-supplemented Mueller-Hinton agar medium (manufactured by Difco Laboratories) for *Enterococcus*, by a serial dilution method according to the standard method as provided by Japanese Society of Chemotherapy. The antibacterial spectra as obtained are shown in Table 5.

TABLE 5

| Microorganisms tested | Tripropeptin D Minimum growth inhibitory concentration (µg/ml) |
|---|---|
| *Staphylococcus aureus* FDA209P | 0.39 |
| *Staphylococcus aureus* Smith | 0.39 |
| *Staphylococcus aureus* MS9610 (multi-drug-resistant) | 0.78 |
| *Staphylococcus aureus* MS16460 (methicillin-resistant) | 1.56 |
| *Staphylococcus aureus* MS16497 (methicillin-resistant) | 0.78 |
| *Staphylococcus aureus* MS16526 (methicillin-resistant) | 0.78 |
| *staphylococcus aureus* TY-00933 (methicillin-resistant) | 0.78 |
| *Staphylococcus aureus* TY-03454 (methicillin-resistant) | 0.78 |
| *Staphylococcus aureus* TY-03456 (methicillin-resistant) | 0.78 |
| *Staphylococcus aureus* TY-04282 (methicillin-resistant) | 0.78 |
| *Micrococcus luteus* FDA16 | 0.20 |
| *Bacillus anthracis* | 1.56 |

TABLE 5-continued

| Microorganisms tested | Tripropeptin D Minimum growth inhibitory concentration (µg/ml) |
|---|---|
| *Bacillus subtilis* PCI219 | 0.78 |
| *Bacillus cereus* ATCC10702 | 1.56 |
| *Corynebacterium bovis* 1810 | 0.20 |
| *Shigella sonnei* JS11746 | >100 |
| *Salmonella typhi* T-63 | >100 |
| *Klebsiella pneumoniae* PCI602 | >100 |
| *Enterococcus faecalis* JCM5803 | 3.13 |
| *Enterococcus faecium* JCM5804 | 6.25 |
| *Enterococcus faecalis* NCTC 12201 (vancomycin-resistant) | 3.13 |
| *Enterococcus faecium* NCTC 12202 (vancomycin-resistant) | 6.25 |
| *Enterococcus faecalis* NCTC 12203 (vancomycin-resistant) | 6.25 |
| *Enterococcus faecium* NCTC 12204 (vancomycin-resistant) | 6.25 |

Further, according to a second aspect of this invention, there is provided a process for the production of antibiotics, tripropeptin Z, tripropeptin A, tripropeptin B, tripropeptin C and/or tripropeptin D represented by the general formula (I) given above, characterized in that the process comprises culturing a microbial strain which belongs to the genus *Lysobacter* and which is capable of producing at least one of tripropeptin Z, tripropeptin A, tripropeptin B, tripropeptin C and tripropeptin D represented by the general formula (I), and recovering at least one of tripropeptins Z, A, B, C and D from the resulting culture.

The microorganism or microbial strain, which is capable of producing the antibiotic, a tripropeptin and is usable in the process according to the second aspect of this invention, may be any strain of those microorganisms which have an ability to produce the said antibiotics that possess the above-mentioned Physico-chemical properties and biological properties, and it can be chosen from a wide variety of microorganisms. Among such usable microorganisms, there may be quoted a bacterial strain to which a strain number BMK333-48F3 is alloted and which was isolated from a soil sample of Naha-city, Okinawa-ken, Japan by our Microbial Chemistry Research Institute in December of 1994, as one preferred concrete example of the microorganism which is capable of producing the antibiotics, tripropeptins.

The microbiological properties of the strain BMK333-48F3 are now described below.

1. Morphology

The strain BMK333-48F3 was a gram-negative rods of which the dimensions of the cell was about 0.5 to 0.8×1.6 to 2.0 µm. Polymorphism of the cell was not observed. The cell did not have flagellum. But the cell had a gliding motility.

2. Growth Characteristics on Various Culture Media

All of the tests were carried out at 30° C., except for broth-gelatin stab culture.

(1) Broth Agar Plate Culture

Colonies were highly viscous, translucent and glossy, and showed pale yellow in color. No diffusible pigment was observed.

(2) Broth Liquid Culture

One day after the start of cultivation, the growth of the strain was slightly observed, but two days after the start of cultivation, the precipitation of the strain was observed at the bottom of the test tube.

(3) Broth Gelatin Stab Culture

In the cultivation at 20° C., liquefaction started from about three days after the start of cultivation and was almost completed in 37 days after the start of cultivation. In the cultivation at 30° C., liquefaction started from 24 hours after the start of cultivation and was completed in 7 days after the start of cultivation.

(4) Milk

Coagulation was observed from about 7 days after the start of the cultivation, and peptonization was completed in 20 days after the start of cultivation. The coagulation proceeded under an acidic condition.

3. Physiological Properties (The Cultivation Temperature was at 30° C. in All Cases, Unless Otherwise Specified)
(1) Gram stain: negative
(2) Reduction of nitrate: positive
(3) Denitrification (according to a method of Komagata et. al.,: Classification and Identification of Microorganisms, edited by Takeji Hasegawa, page 223, University of Tokyo press, 1975): negative
(4) MR teat: negative
(5) V-P test: negative
(6) Production of indole: negative
(7) Production of hydrogen sulfide: negative
(8) Utilization of citric acid:
   On Koser medium, negative
   On Christensen medium, negative
(9) Utilization of inorganic nitrogen sources:
   For sodium nitrate, negative
   For ammonium sulfate, negative
(10) Formation of pigment:
   No soluble pigment was observed either on King A medium or on King B medium.
(11) Urease (in a urea medium, provided from Eiken Chemical):
   negative
(12) Oxidase: positive
(13) Catalase: positive
(14) Range of growth:
   The growth of the strain was observed at a pH in a range of pH 6.0 to 9.0 and the optimal pH is 6.0 to 8.0. Furthermore, the growth of the strain was observed at a temperature in a range of 27° C. to 37° C. and the optimal growth temperature was 24° C. to 30° C.
(15) Behavior for oxygen: aerobic
(16) O-F test (according to Hugh Leifson method):
   Slightly oxidative form
(17) The formation of acids and gases from saccharides (in the basal medium):
   From glucose, arabinose, maltose and trehalose, the production of a small amount of acids was observed. However, from D-xylose, D-mannose, D-fructose, D-galactose, sucrose, D-sorbitol, D-mannitol, inositol, glycerol and starch, the production of any acid was not observed. In addition, the production of gases was not observed from any of the saccharides.
(18) Hydrolysis of casein: positive
(19) Hydrolysis of esculin: positive
(20) Acid fastness: Non fast to acid 4. Chemotaxonomic Properties (1) Base Composition (G+C Content) of DNA: 70.5%
Summarizing the above-mentioned properties of the strain BMK333-48F3, this strain was characterized in that it was an aerobic gram-negative rods, did not have flagella and spores, had a gliding motility and was not fast to acid; that the growth of the strain on the agar medium was translucent and highly viscous; that the dimensions of the cell were about 0.5 to 0.8×1.6 to 2.0 µm; that the strain grew at a pH in the range of pH 6 to 9; that the strain grew at a temperature in the range of 27° C. to 37° C. and the optimum growth temperature was 24° C. to 30° C.; and that the strain had a (G+C) content of its DNA which was 70.5%.

In view of these properties above, it is presumed that the strain BMK333-48F3 belongs to the genus *Lysobacter*. So, we have designated the strain BMK333-48F3 as *Lysobacter* sp. BMK333-48F3.

Furthermore, the strain BMK333-48F3 has been deposited in an authorized Japanese depository, the National Institute of Bioscience and Human-Technology, Advanced Industrial Science and Technology, Agency of Ministry of Economy, Trade and Industry, located at No. 1-3, Higashi 1-chome, Tsukuba-City, Ibaraki-ken, Japan, under the deposit number of FERMP-17741 on Feb. 22, 2000. This strain has now been deposited under the deposit number "FERM BP-7477" since Mar. 2, 2001 in said National Institute as transferred in terms of the Budapest Treaty.

According to the second aspect process of this invention, the production of the antibiotic, a tripropeptin may be carried out as described below.

Thus, the production of the antibiotic, a tripropeptin may be carried out by inoculating a microbial strain capable of producing a tripropeptin, preferably the strain *Lysobacter* sp. BMK333-48F3 to a nutrient medium, and cultivating said microbial strain at a temperature of 27° C. with shaking under aerobic conditions, to afford the culture containing the antibiotic tripropeptins. As the nutrient medium to be used for this purpose, there may be used any nutrient medium which is usable for the cultivation of microorganisms. As the nutrient sources, there may be used the nitrogen sources such as peptone, yeast extract, meat extract, cotton seed meal and ammonium sulfate which are commercially available. As the carbon sources, there may be used carbohydrates such as glycerin, starch, glucose, galactose, dextrin and fats. Further, there may be used inorganic salts such as sodium chloride and calcium carbonate, as additives. If necessary, other additives, for example, metal salts may be added in very small amounts. These additive substances may be any of those materials which are utilized by a tripropeptin-producing strain and are useful for the production of the antibiotic tripropeptins, and which are known to be utilizable in the culture media for the cultivation of microorganisms.

For the production of the antibiotic tripropeptins, there may be used a microorganism having an ability to produce the antibiotic tripropeptins. Specifically, the strain *Lysobacter* sp. BMK333-48F3 as isolated by us has been confirmed to produce the antibiotic tripropeptins. Any other strain capable of producing said antibiotics is possible to be isolated from the nature by employing any known isolation technique which are available for the isolation of the antibiotic-producing strains. There is still available such technique by which the ability of a tripropeptin-producing strain, including the strain *Lysobacter* sp. BMK333-48F3, to produce the antibiotic tripropeptins is improved by subjecting such strain to a mutation treatment with radio-active radiation or others. Further, the antibiotic tripropeptins may be produced by a genetic engineering technique.

The antibiotics, tripropeptins are produced by cultivating aerobically a tripropeptin-producing strain belonging to the genus *Lysobacter* in a suitable culture medium, and collecting the desired tripropeptin(s) from the resulting culture broth. The cultivation temperature may be in the range of temperatures at which the desired antibiotics can be produced without substantially preventing the growth of the tripropeptin-producing strain as used. The cultivation temperature may be chosen properly depending upon the nature of a tripropeptin-producing strain as used, and a preferred cultivation temperature is in a range of 25 to 30° C.

The production of the antibiotic tripropeptins by the strain BMK333-48F3 can usually reach a maximum in 2 to 4 days of the cultivation of the strain. In general, however, the cultivation of the strain is continued until a sufficient antibacterial activity is imparted to the culture medium. The time-dependent change in the titer of tripropeptins in the resulting culture broth may be measured either by HPLC method, or by a cylinder plate method in which *Staphylococcus aureus* or *Bacillus stearothermophilus* is used as an assaying strain.

In the second aspect process of this invention, tripropeptins are recovered from the culture broth which has been obtained as above and in which tripropeptins have been produced and accumulated. As the method for recovering and isolating the desired tripropeptin(s), there may appropriately be used any of routine methods which are conventionally used for the isolation of metabolite(s) as produced by microorganisms. For example, a method for extraction with an organic solvent immiscible with water, and a method for utilizing the difference in the adsorption affinities of the tripropeptins onto various adsorbents, such as a method for gel filtration and chromatographic method with countercurrent distribution, etc., may be used, singly or in combination, in order to recover tripropeptin(s) from the culture broth supernatant. Further, from the microbial cells of the strain so separated from the culture broth, it is possible to recover tripropeptin(s) by subjecting the microbial cells to a solvent extraction with a suitable organic solvent, or by a method comprising disrupting the microbial cells and eluting the desired tripropeptin(s) out of the disrupted cells by extraction; and then it is possible to isolate and purify the so recovered tripropetin(s). Thus, one or more of the antibiotic tripropeptins may be harvested. Incidentally, the isolation of tripropeptins Z, A, B, C and D from each other may be effected by a column chromatography (refer to Example 1 as described below).

Further, according to a third aspect of this invention, there is provided a pharmaceutical composition which comprises as an active ingredient at least one of tripropeptins Z, A, B, C and D represented by the general formula (I) or a pharmaceutically acceptable salt thereof, in admixture with a pharmaceutically acceptable carrier or carriers.

The pharmaceutical composition according to the third aspect of this invention may be in the form of a composition which comprises as the active ingredient a compound of the general formula (I), in admixture with a conventional, pharmaceutically acceptable solid or liquid carrier, for example, starch, sugar, ethanol, water, physiological saline and so on.

Tripropeptin(s) of the general formula (I) or a salt thereof, which is or are to be used in the pharmaceutical composition according to the third aspect of this invention, may be administered orally or parenterally by intravenous, intramuscular or subcutaneous injection or by intraperitoneal or intrarectal administration and so on.

For the oral administrations, the pharmaceutical composition according to the third aspect of this invention may be formulated in the form of preparations such as powder, tablets, capsules, suspension, syrup and the like, by blending the active ingredient, namely a tripropeptin of general formula (I) or a salt thereof, with a conventional, pharmaceutically acceptable solid or liquid carrier.

The proportion of the compound of the general formula (I) which is incorporated as the active ingredient in the pharmaceutical composition of the third aspect of this invention may vary depending upon the type of the preparations, but a convenient proportion of a tripropeptin may be in the range of about 2 to 90%, based on the weight of the single dosage unit of the composition.

In cases where the composition of the third aspect of this invention is formulated into injections, a preferred form of the injectable preparations may include a sterilized aqueous solution or a sterilized and lyophilized preparation which contains the compound of the general formula (I) as an active ingredient. As examples of the liquid carriers usable for this purpose, are preferred water, physiological saline, aqueous ethanol, glycerol, propylene glycol, vegetable oil and the like.

The dose of a tripropeptin of the general formula (I) or a salt thereof used as an active ingredient in the composition of this invention may vary depending upon the nature of bacterial infections to be treated, a purpose of the therapeutic treatment, degree of the patient's conditions and so on. However, an optimal dose of a tripropeptin can be decided by experts through suitable preliminary tests. By the way, tripropeptin C did not exhibit any toxicity in mice (ICR type, 4 weeks-aged, male), when it is administered intravenously at a dose of 300 mg/kg.

According to a fourth aspect of this invention, there is further provided, as a novel microorganism, a strain *Lysobacter* sp. BMK333-48F3 which has a characteristic nature that it is capable of producing tripropeptins of general formula (I) above, and which is identifiable as the strain which has been deposited in a Japanese depository, the National Institute of Bioscience and Human-Technology, Advanced Industrial Science and Technology, Agency of Ministry of Economy, Trade and Industry, under the deposit number of FERM BP-7477 in terms of the Budapest Treaty.

BRIEF DESCRIPTION OF ATTACHED DRAWINGS

BEST MODE FOR CARRYING OUT THE INVENTION

Figure 1:
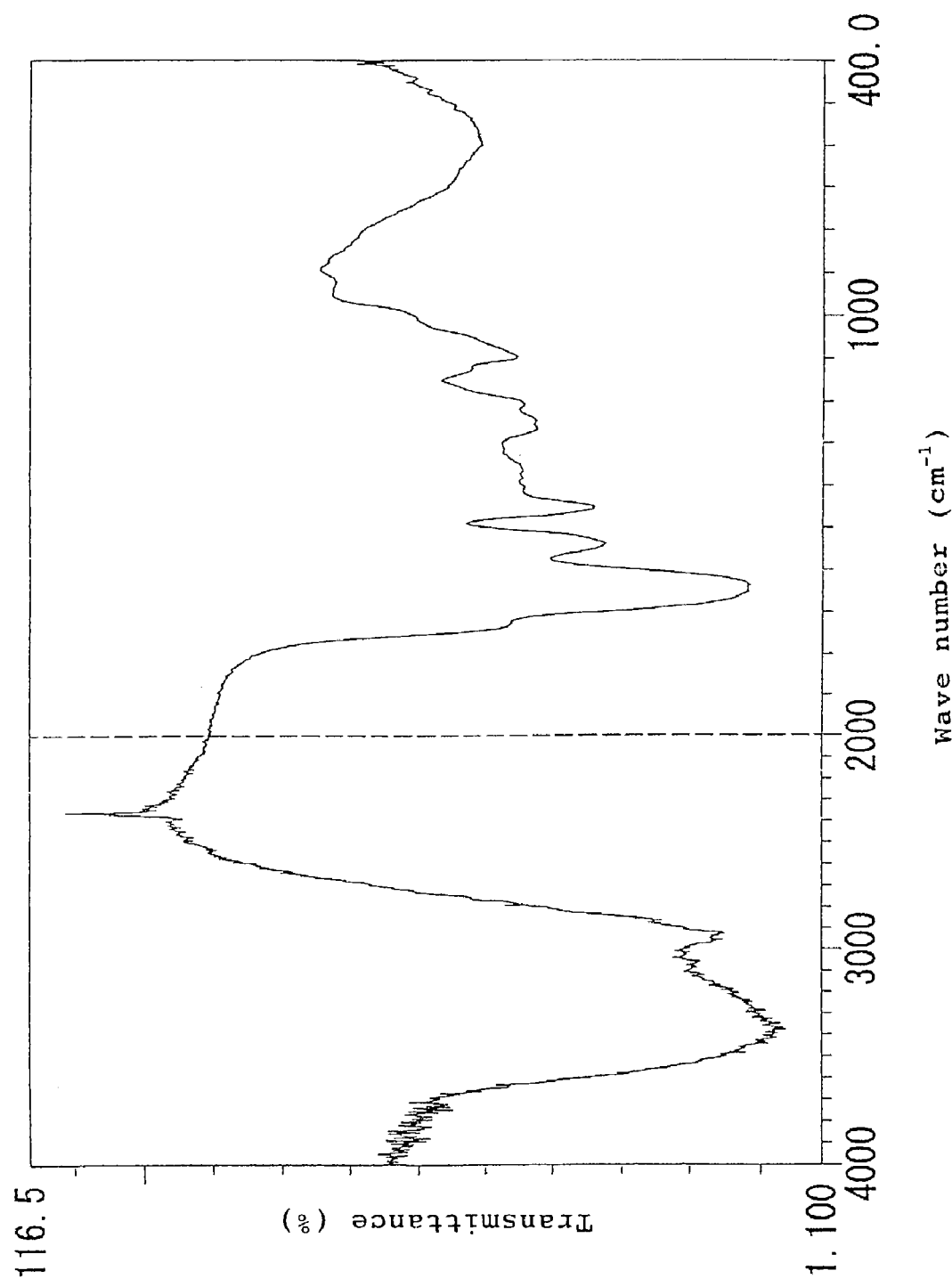
FIG. 1 is an infrared absorption spectrum of tripropeptin Z as measured by the KBr tablet method.
Figure 2:
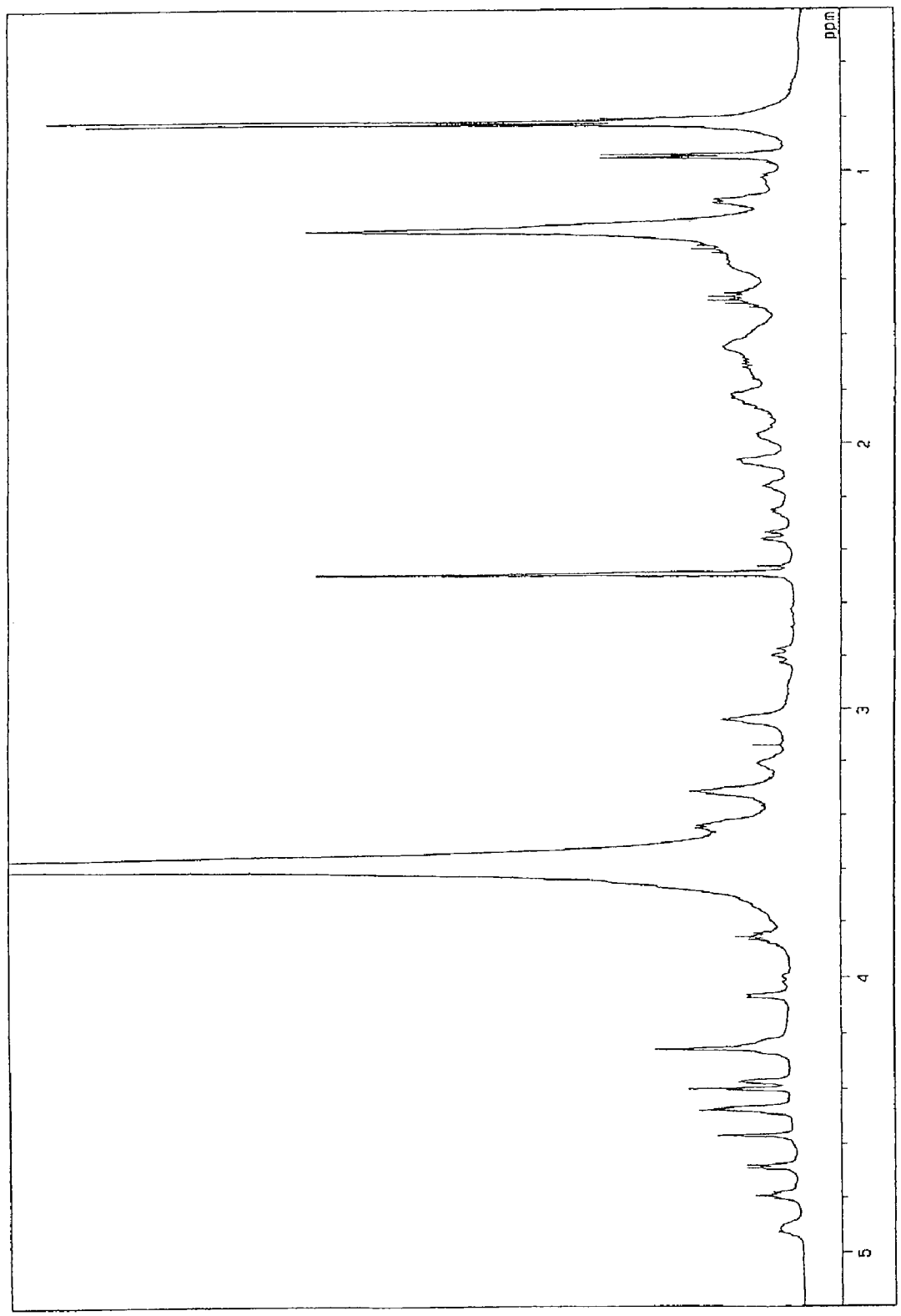
FIG. 2 is a proton nuclear magnetic resonance spectrum of tripropeptin Z as measured in a solution in DMSO-$d_6$-$D_2O$ (20:1) at 500 MHz at room temperature.
Figure 3:
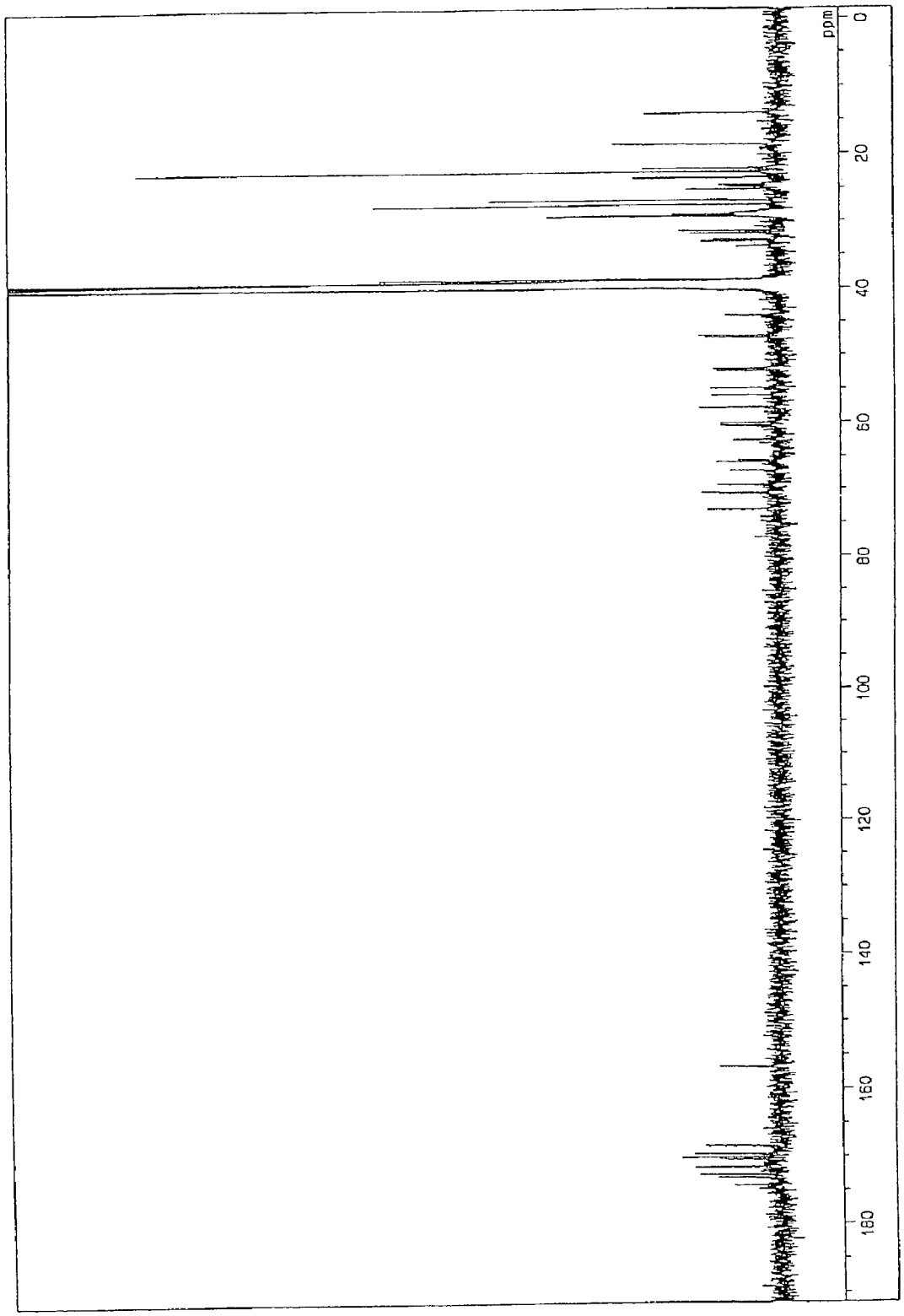
FIG. 3 is $^{13}C$-nuclear magnetic resonance spectrum of tripropeptin Z as measured in a solution in DMSO-$d_6$-$D_2O$ (20:1) at 125 MHz at room temperature.
Figure 4:
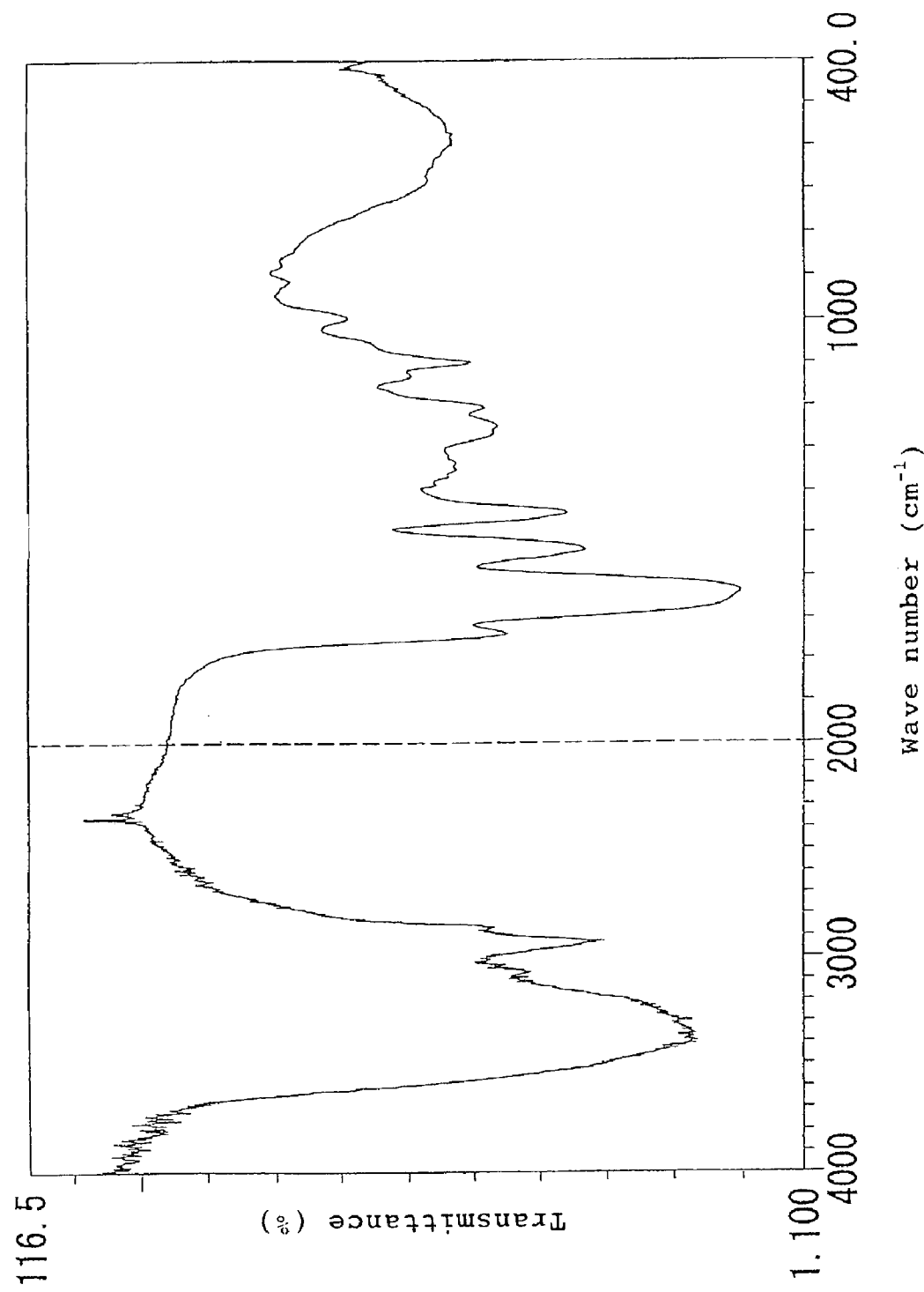
FIG. 4 is an infrared absorption spectrum of tripropeptin A as measured by the KBr tablet method.
Figure 5:
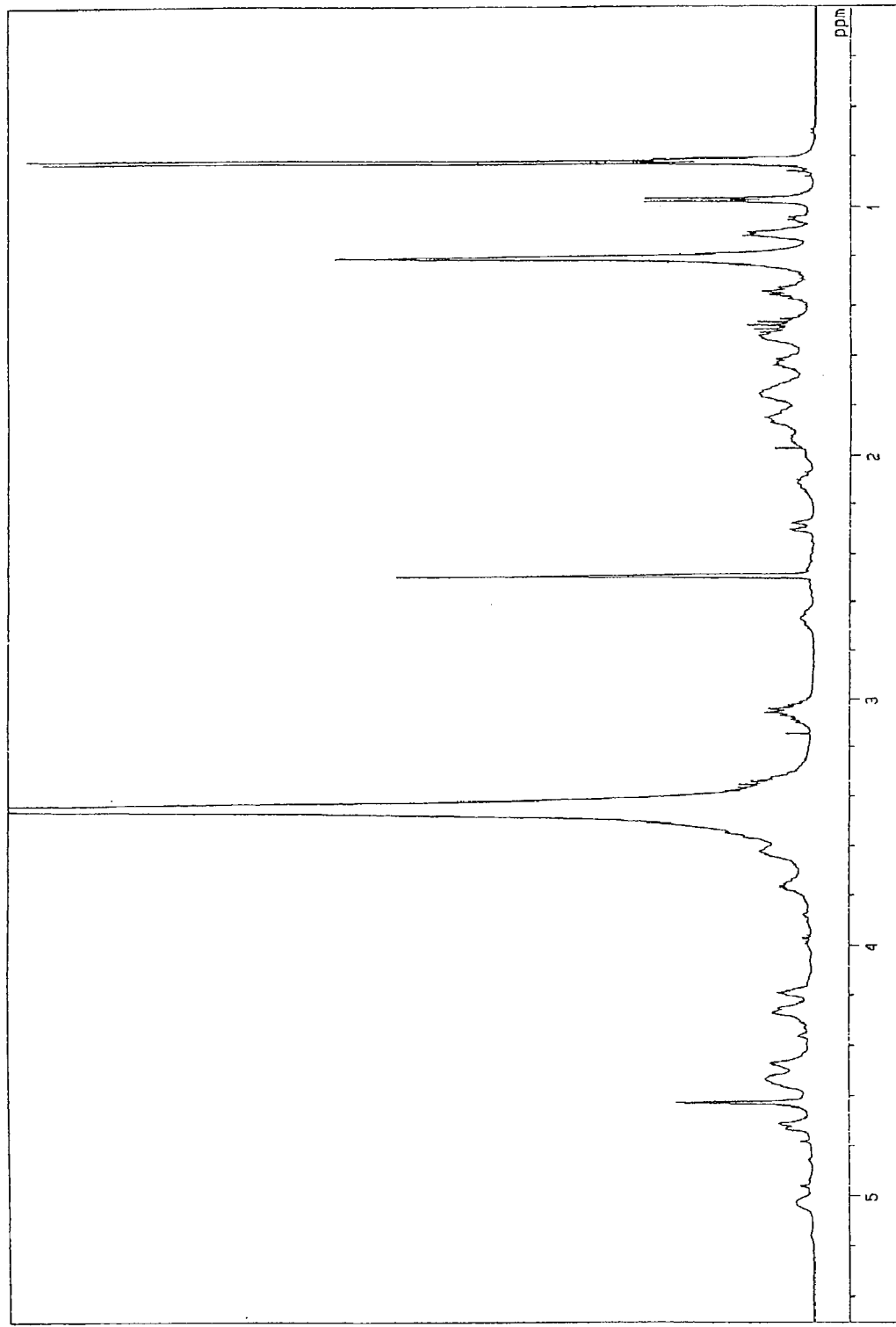
FIG. 5 is a proton nuclear magnetic resonance spectrum of tripropeptin A as measured in a solution in DMSO-$d_6$-$D_2O$ water (20:1) at 500 MHz at room temperature.
Figure 6:
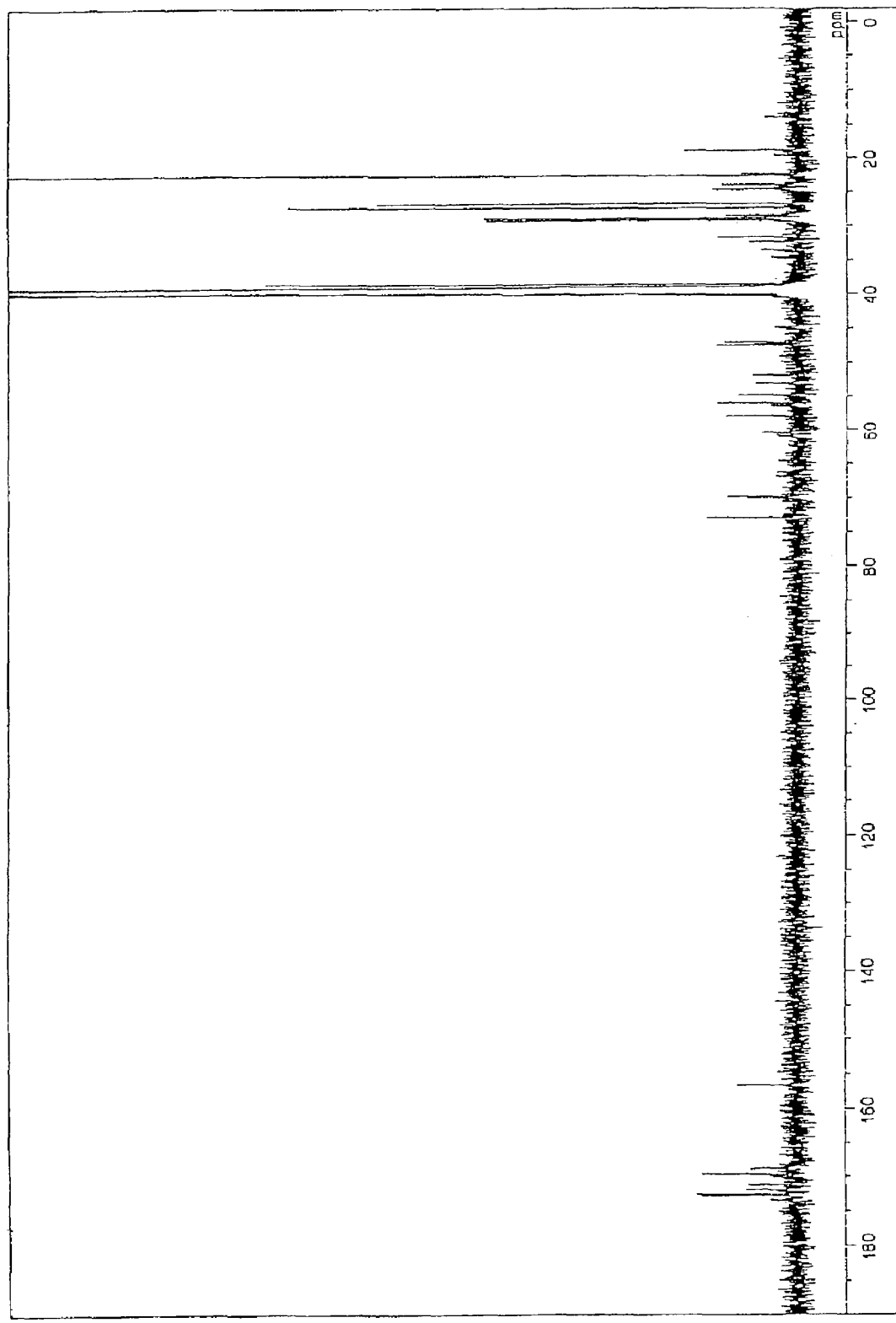
FIG. 6 is a $^{13}C$-nuclear magnetic resonance spectrum of tripropeptin A as measured in a solution in DMSO-$d_6$-$D_2O$ (20:1) at 125 MHz at room temperature.
Figure 7:
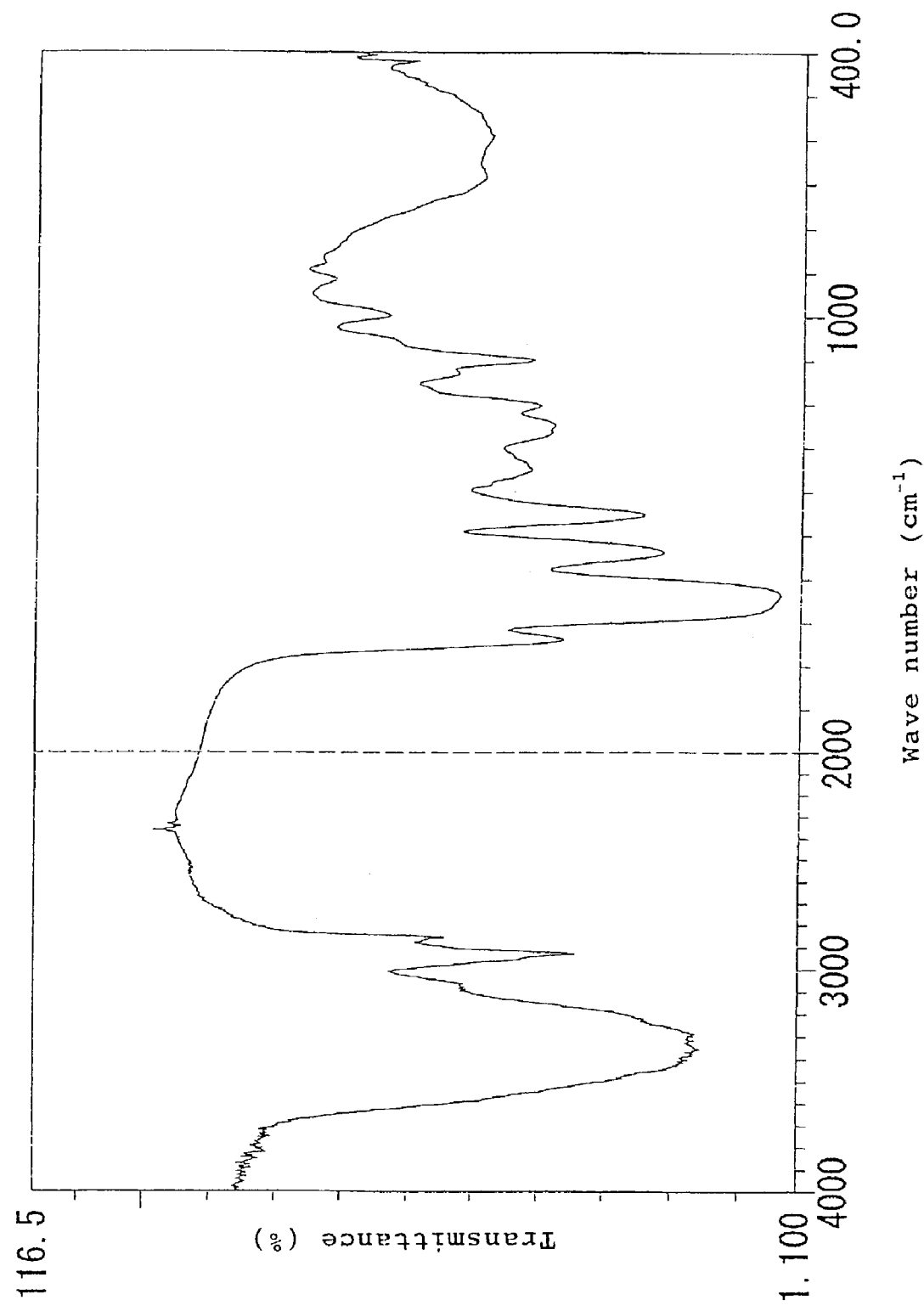
FIG. 7 is an infrared absorption spectrum of tripropeptin B as measured by the KBr tablet method.
Figure 8:
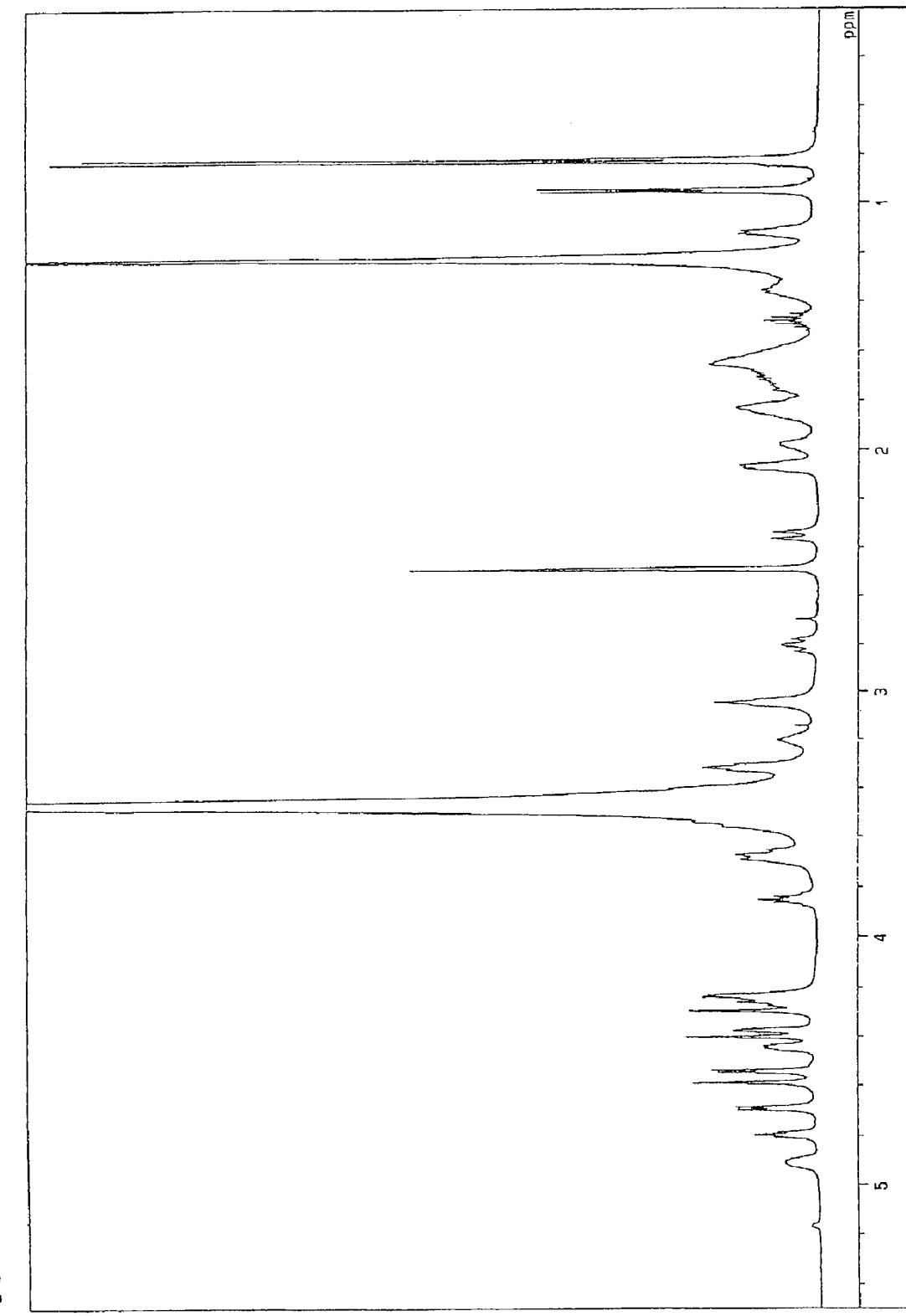
FIG. 8 is a proton nuclear magnetic resonance spectrum of tripropeptin B as measured in a solution in DMSO-$d_6$-$D_2O$ (20:1) at 500 MHz at room temperature.
Figure 9:
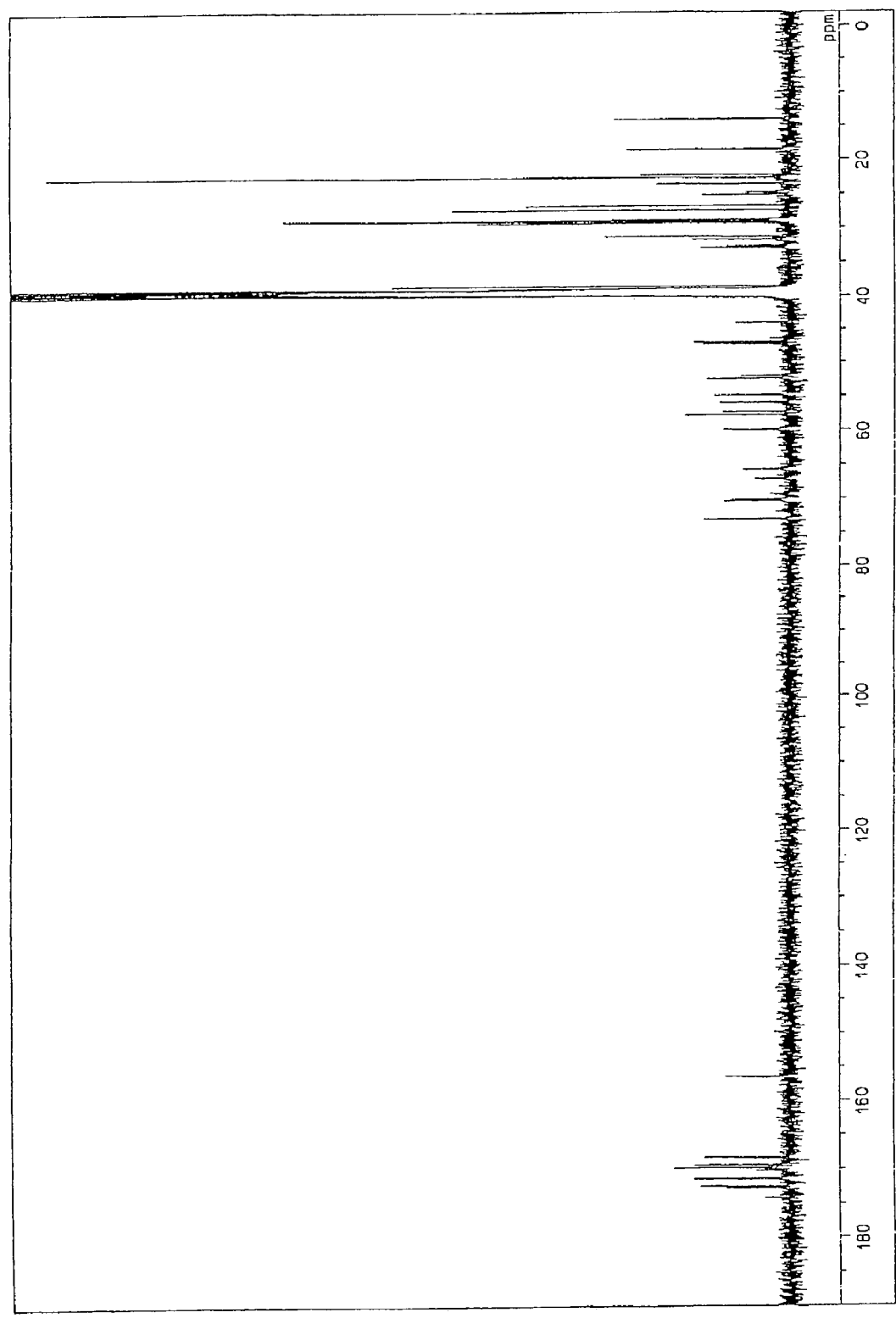
FIG. 9 is a $^{13}C$-nuclear magnetic resonance spectrum of tripropeptin B as measured in a solution in DMSO-$d_6$-$D_2O$ (20:1) at 125 MHz at room temperature.
Figure 10:
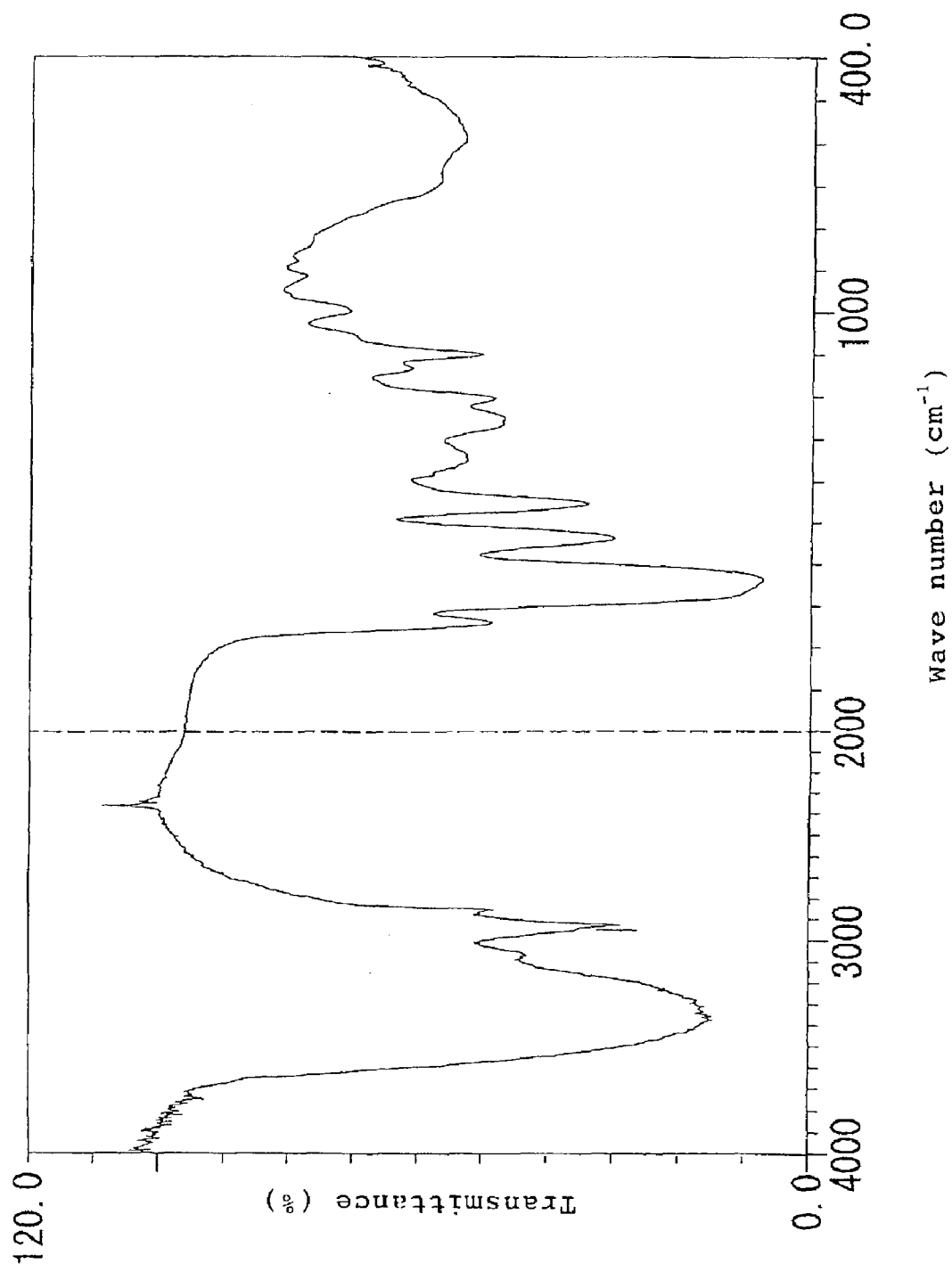
FIG. 10 is an infrared absorption spectrum of tripropeptin C as measured by the KBr tablet method.
Figure 11:
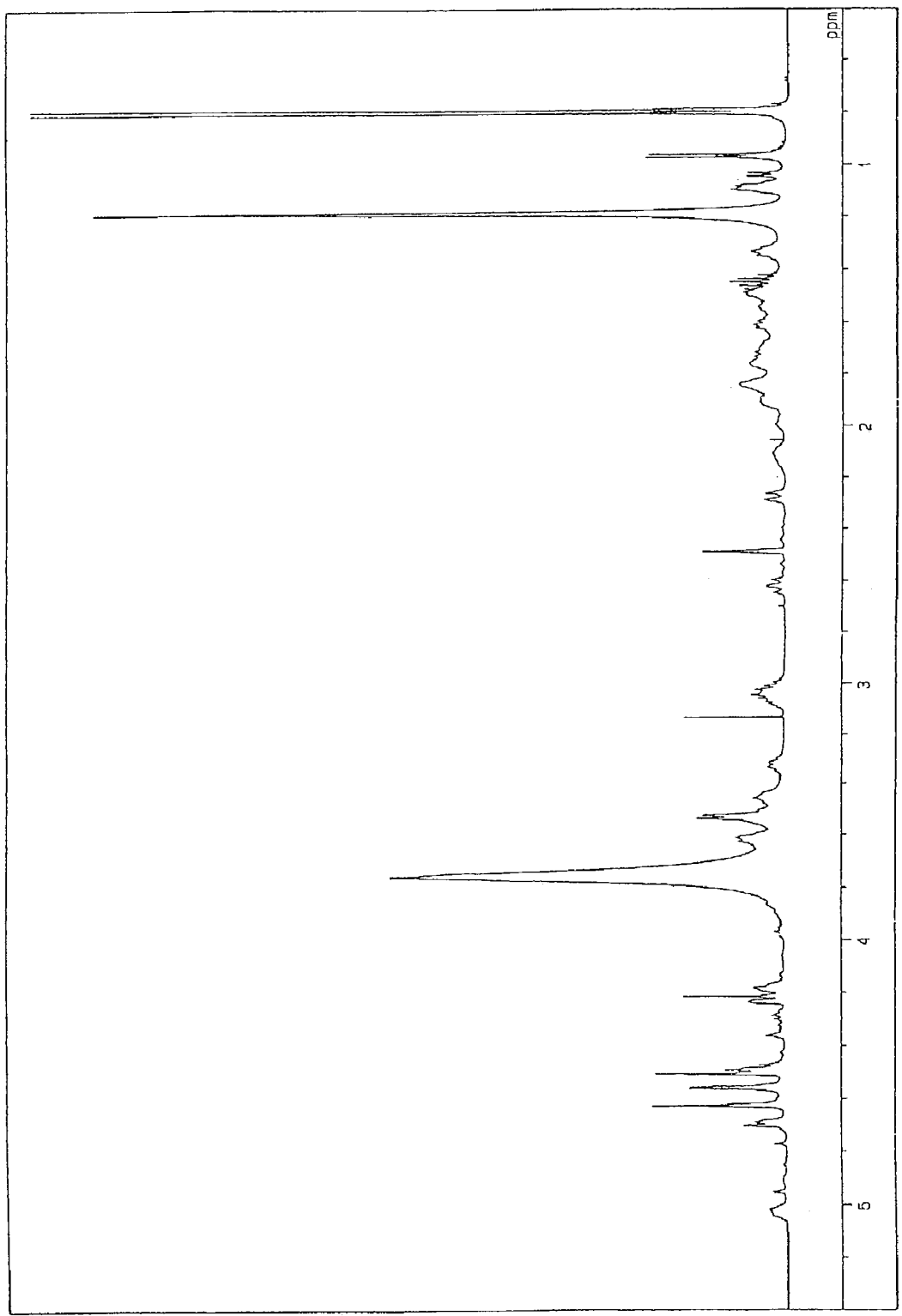
FIG. 11 is a proton nuclear magnetic resonance spectrum of tripropeptin C as measured in a solution in DMSO-$d_6$-$D_2O$ 20:1) at 500 MHz at room temperature.
Figure 12:
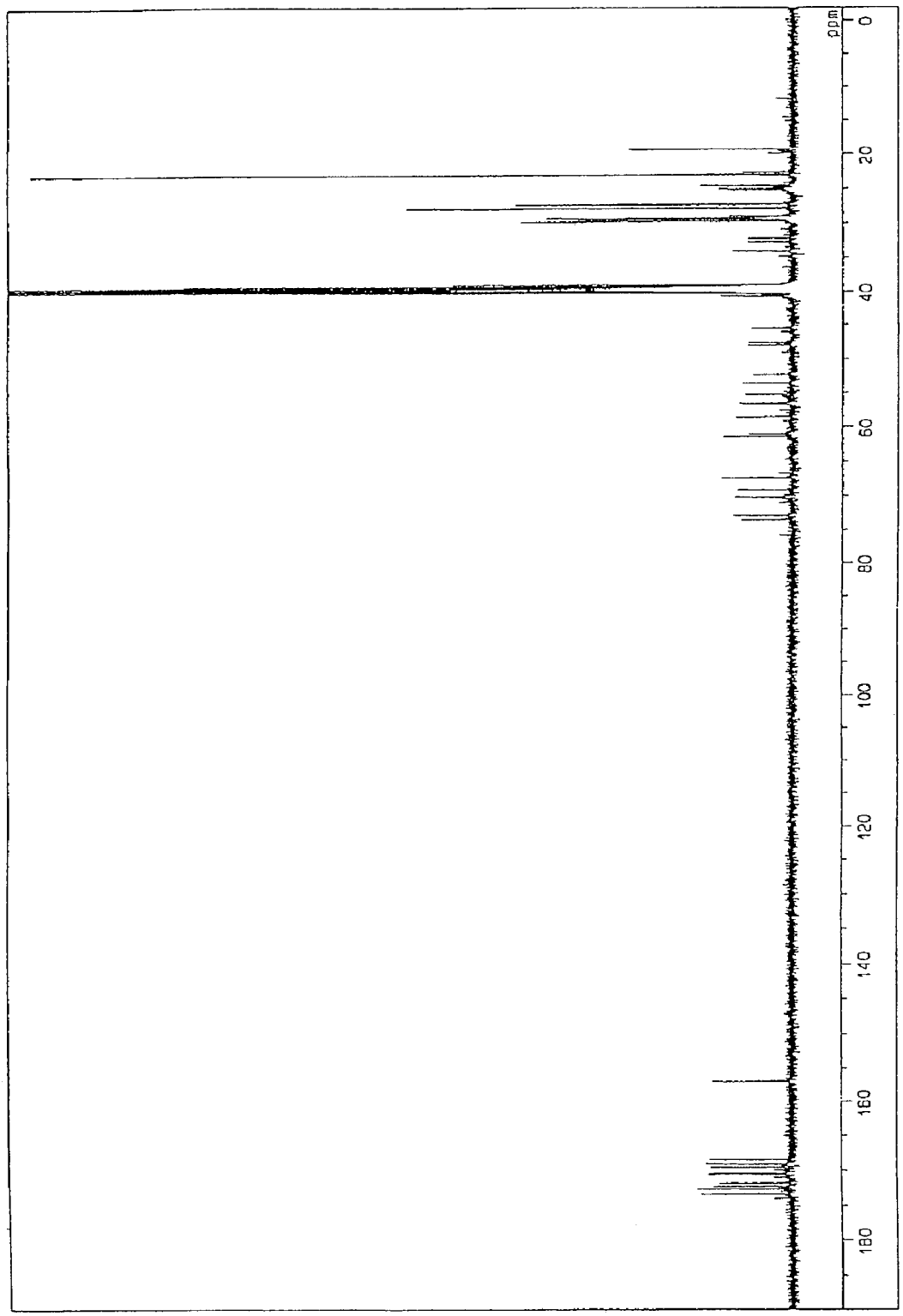
FIG. 12 is a $^{13}C$-nuclear magnetic resonance spectrum of tripropeptin C as measured in a solution in DMSO-$d_6$-$D_2O$ (20:1) at 125 MHz at room temperature.
Figure 13:
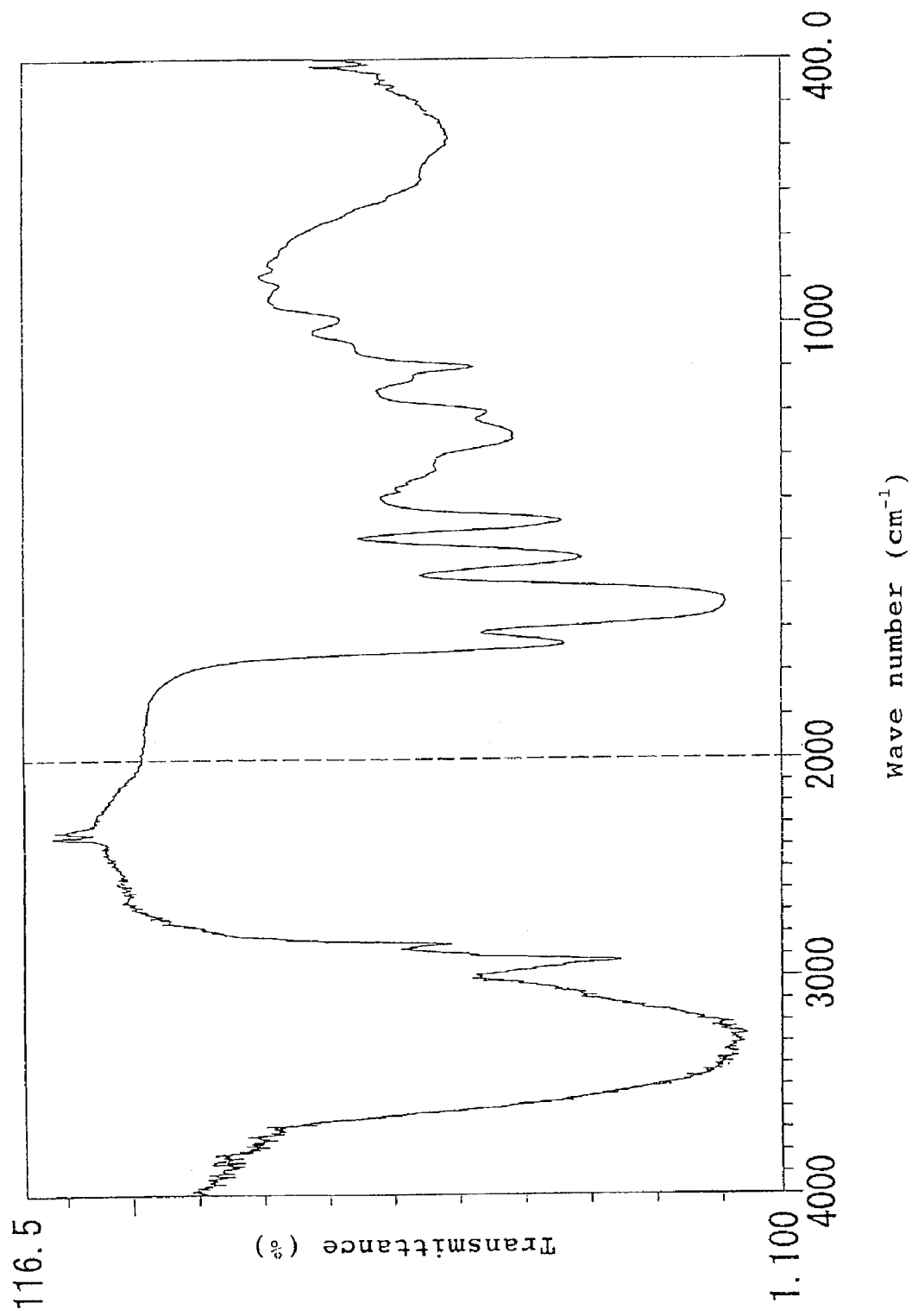
FIG. 13 is an infrared absorption spectrum of tripropeptin D as measured by the KBr tablet method.
Figure 14:
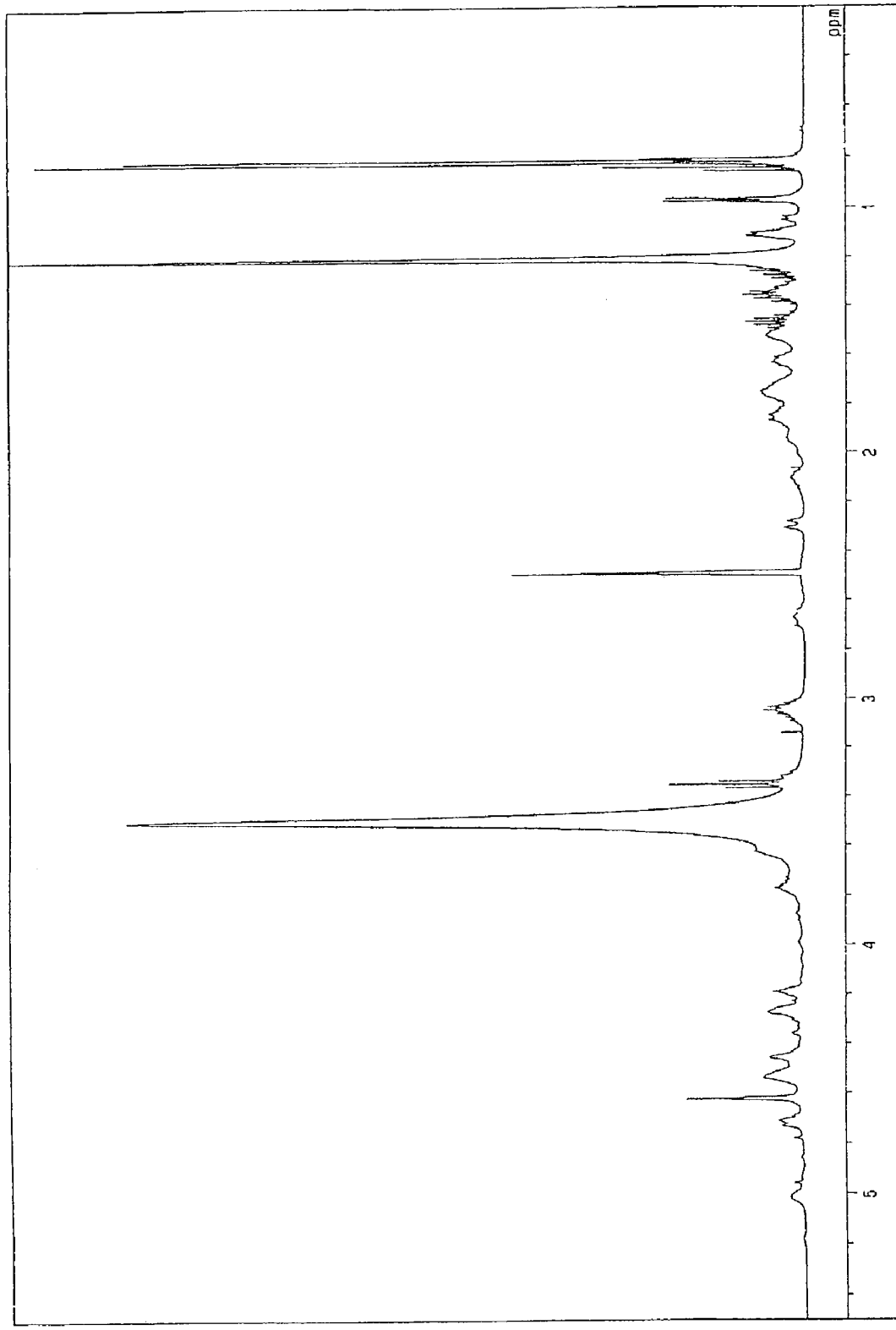
FIG. 14 is a proton nuclear magnetic resonance spectrum of tripropeptin D as measured in a solution in DMSO-$d_6$-$D_2O$ (20:1) at 500 MHz at room temperature.
Figure 15:
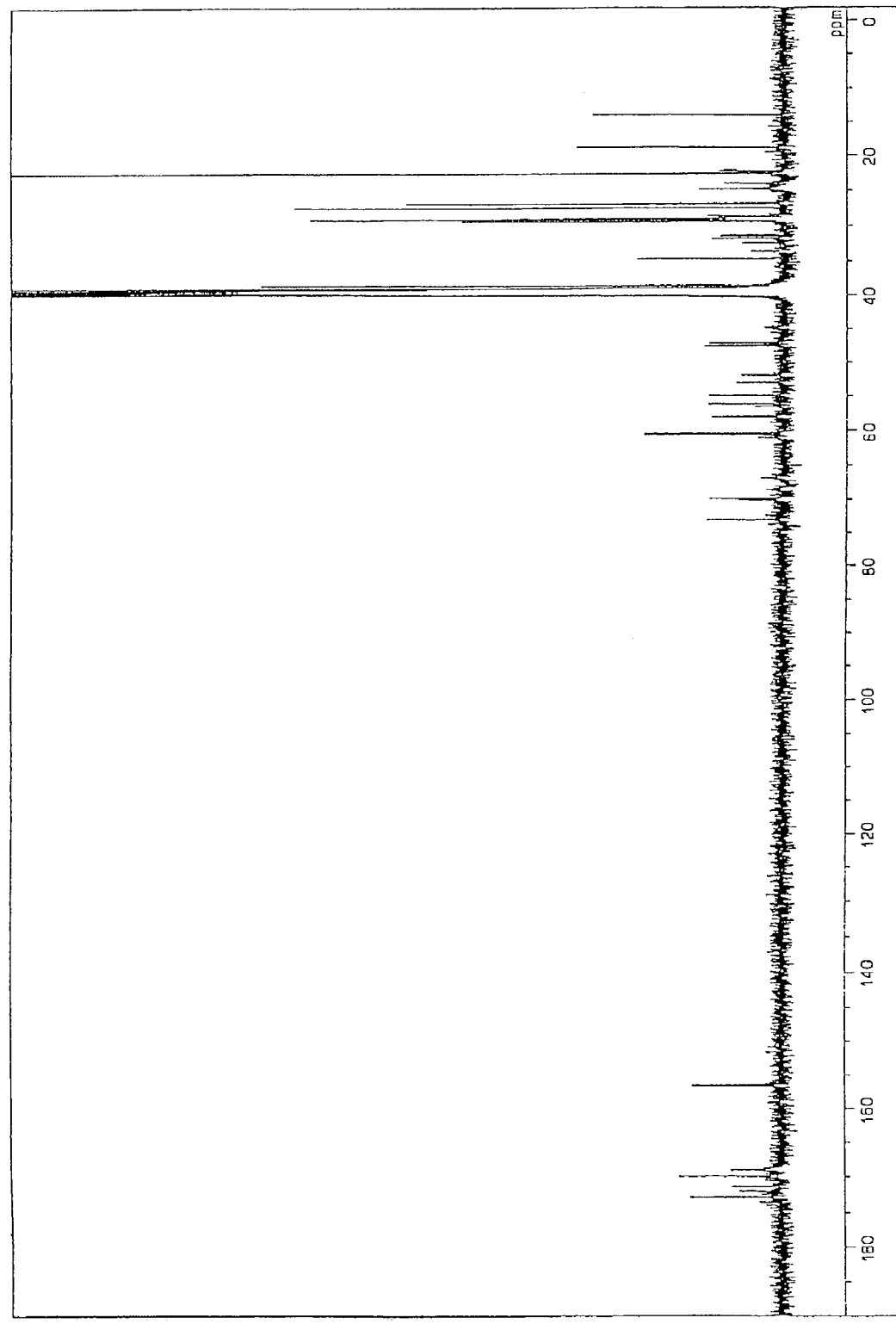
FIG. 15 is a $^{13}C$-nuclear magnetic resonance spectrum of tripropeptin D as measured in a solution in DMSO-$d_6$-$D_2O$ (20:1) at 125 MHz at room temperature.

This invention is now illustrated in more detail with reference to the following Example.

EXAMPLE 1

Production of the Antibiotic Tripropeptins

A strain, Lysobacter sp. BMK333-48F3 (deposited under the access number of FERM BP-7477), which had been cultured on agar slant culture medium, was inoculated to a sterile culture medium. The sterile culture medium used here had been prepared by placing into Erlenmeyer flasks (of 500 ml-capacity each) 110 ml-portions of a liquid culture medium comprising 1.5% glycerin, 1.5% cotton seed meal, 0.3% sodium chloride and 0.5% sodium L-glutamate (adjusted a pH of 7.4) and sterilizing the culture medium in the flasks in a usual manner, before the inoculation of the strain BMK333-48F3 was done. The liquid culture medium so inoculated was then incubated with shaking at 27° C. for 24 hours, thereby to afford a seed culture broth as intended.

Furthermore, into Erlenmeyer flasks (of 500 ml-capacity each) were placed 110 ml-portions of a liquid culture medium comprising 1.5% glycerin, 1.5% cotton seed meal, 0.3% sodium chloride and 0.5% sodium L-glutamate (adjusted a pH of 7.4), followed by and sterilizing in a usual manner. The liquid culture medium thus prepared was used as a productive culture medium. To 50 liter of this productive culture medium was inoculated a 2% proportion of the above-mentioned seed culture broth, and then the shaking cultivation was made with rotation at 27° C. for 2 days.

The culture broth thus obtained was centrifuged to separate into the culture broth filtrate and the cultured microbial cells. The cultured microbial cells were extracted with 10 liter of methanol and thereafter the methanolic extract was concentrated under reduced pressure. The resulting concentrated solution was combined together with the said culture broth filtrate, and 50 liter of the resulting mixture was passed through a column comprising 6 liter of a synthetic adsorbent resin made of a porous polystytene-divinylbenzene copolymer, namely "Diaion HP-20" resin (a product of Mitsubishi Chemical Co., Japan), whereby the tripropeptins were adsorbed in the Diaion HP-20 resin. Through this Diaion HP-20 resin column containing the adsorbed tripropeptins, were passed each 18 liters of deionized water, 50% aqueous methanol and 65% aqueous acetone, in order. The eluate as obtained by eluting said column with the 65% aqueous acetone, is an active fraction, and this eluate was concentrated to dryness under reduced pressure, whereby 30 g of a solid extract containing tripropeptins was obtained. This crude solid extract containing tripropeptins was placed on the top of a silica gel column (commercially available from Merck Co., USA) (1500 ml) and chromatographed successively with solvent mixtures of chloroform-methanol-water (10:5:1) and butanol-methanol-water (4:1:2). These active fractions were collected and concentrated, whereby 10.8 g of a solid partially purified product containing tripropeptins was obtained. This partially purified product was taken up into 50% aqueous methanol and the resulting solution was passed through a column (250 ml) comprising an aromatic, synthetic adsorbent resin, "Diaion CHP20P" resin (a product of Mitsubishi Chemical Co., Japan), whereby the tripropeptins were adsorbed in the Diaion CHP20P resin. Through this Diaion CHP20P resin column containing the adsorbed tripropeptins, were successively passed each 750 ml of 20% aqueous acetone, 30% aqueous acetone, 35% aqueous acetone, 40% aqueous acetone, 45% aqueous acetone, 50% aqueous acetone, 55% aqueous acetone and 60% aqueous acetone.

The fraction as obtained by eluting said column with the 40% aqueous acetone was concentrated under reduced pressure to afford 65.7 mg of tripropeptin Z. The fraction as obtained by eluting said column with the 45% aqueous acetone was concentrated under reduced pressure to afford 189.7 mg of tripropeptin A. Some of the fractions as obtained by eluting said column with the 45% aqueous acetone to 50% aqueous acetones was concentrated under reduced pressure to afford 210.6 mg of tripropeptin B. Similarly, another some of the fractions as obtained by eluting with the 45% aqueous acetone to 50% aqueous acetone was concentrated under reduced pressure to afford 1.0 g of tripropeptin C. The fraction as obtained by eluting with the 50% aqueous acetone was concentrated under reduced pressure to afford 50.1 mg of tripropeptin D.

INDUSTRIAL APPLICABILITY

As described hereinbefore, tripropeptins Z, A, B, C and D having the general formula (I) each are provided as the novel antibiotics according to this invention. The tripropeptins each have excellent antibacterial activities against various gram-positive bacteria and their drug-resistant strains. Therefore, a tripropeptin according to this invention is useful as an antibiotic agent effective for treating bacterial infections including their drug-resistant strains.

The invention claimed is:

1. An isolated antibiotic which is at least one of tripropeptin Z tripropeptin A, tripropeptin B, tripropeptin C or tripropeptin D, and is a compound represented by the general formula (I):

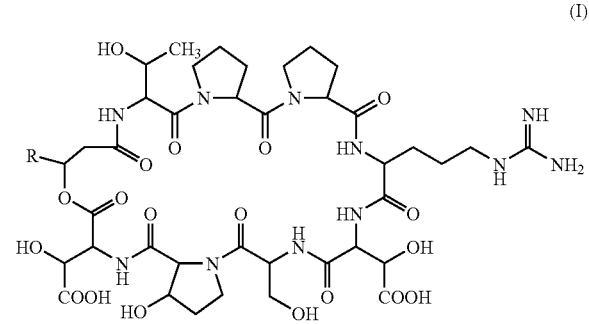

(I)

wherein R is 7-methyl-octyl group for tripropeptin Z; 8-methyl-nonyl group for tripropeptin A; 9-methyl-dodecyl group for tripropeptin B; 10-methyl-undecyl group for tripropeptin C; 11-methyl-dodecyl group for tripropeptin D, or a pharmaceutically acceptable salt thereof.-

2. An antibiotic as claimed in claim 1, which is tripropeptin Z represented by the formula (Iz):

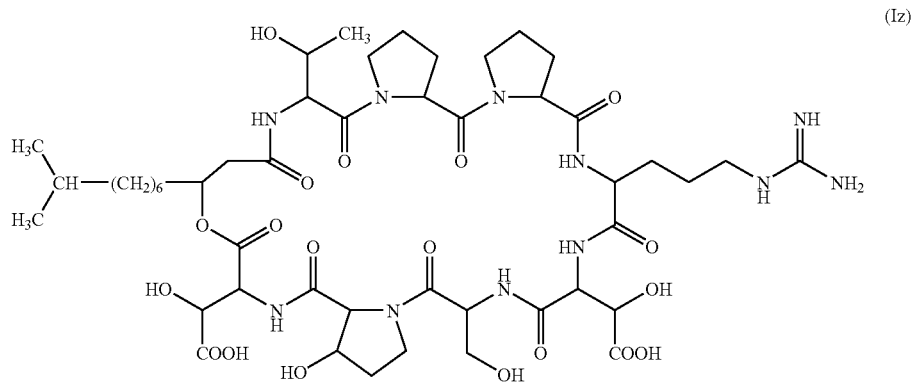

(Iz)

that is, the compound of the general formula (I) shown in claim 1 where R is 7-methyl-octyl group.

3. An antibiotic as claimed in claim 1, which is tripropeptin A represented by the formula (Ia):

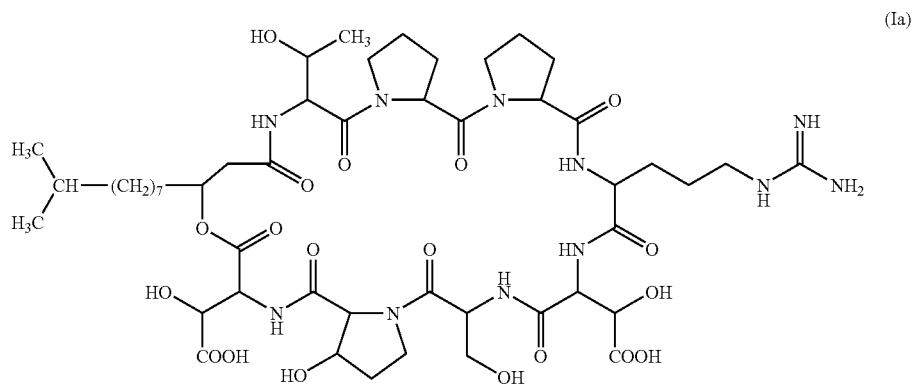

(Ia)

that is, the compound of the general formula (I) shown in claim 1 where R is 8-methyl-nonyl group.

4. An antibiotic as claimed in claim 1, which is tripropeptin B represented by the formula (Ib):

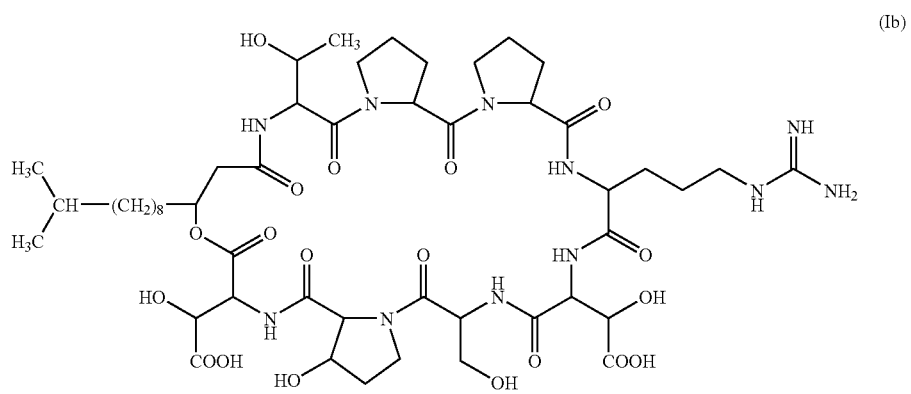

(Ib)

that is, the compound of the general formula (I) shown in claim 1 where R is 9-methyl-decyl group.

5. An antibiotic as claimed in claim 1, which is tripropeptin C represented by the formula (Ic):

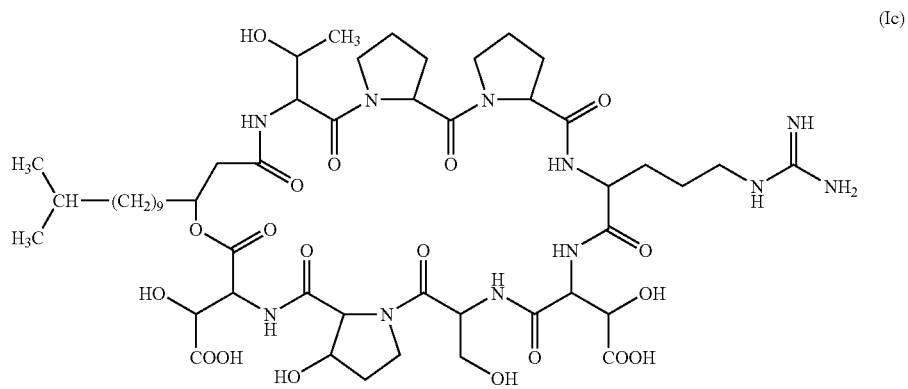

(Ic)

that is, the compound of the general formula (I) shown in claim 1 where R is 10-methyl-undecyl group.

6. An antibiotic as claimed in claim 1, which is tripropeptin D represented by the formula (Id):

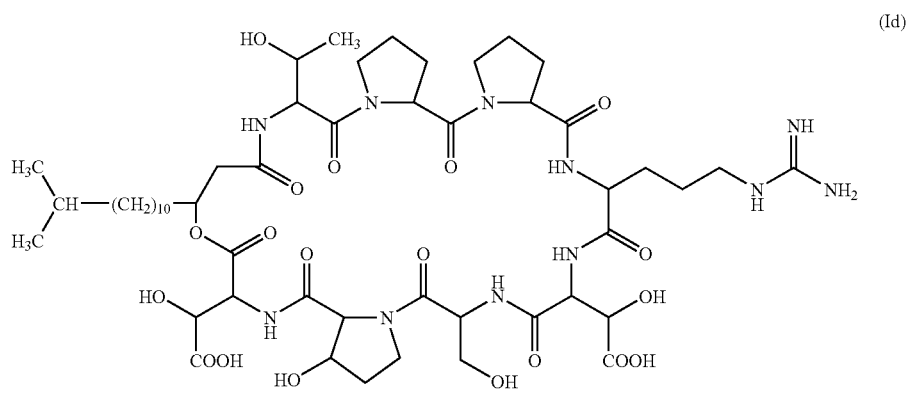

(Id)

that is, the compound of the general formula (I) shown in claim 1 where R is 11-methyl-dodecyl group.

7. A process for the production at least one of the antibiotics, tripropeptin Z, tripropeptin A, tripropeptin B, tripropeptin C and/or tripropeptin D represented by the general formula (I) given in claim 1, which comprises culturing *Lysobacter* sp. BMK 333-48F3 which has been deposited in the National Institute of Bioscience and Human-Technology of Advanced Industrial Science and Technology, Agency of Ministry of Economy, Trade and Industry, under the deposit number of FERM BP-7477 and which is capable of producing at least one of the antibiotics, tripropeptin Z, tripropeptin A, tripropeptin B, tripropeptin C and tripropeptin D, and recovering at least one of tripropeptins Z, A, B, C and D from the resulting culture.

8. A pharmaceutical composition comprising, as an active ingredient, at least one of tripropeptins Z, A, B, C and D having the general formula (I) given in claim 1, or a pharmaceutically acceptable salt thereof, in admixture with a pharmaceutically acceptable carrier or carriers.

9. A composition as claimed in claim 8, which is an antibacterial composition.

10. An isolated and biologically pure culture of a strain *Lysobacter* sp. BMK333-48F3 which has a characteristic nature that it is capable of producing tripropeptins Z, A, B, C and D having the general formula (I) given in claim 1, and which has been deposited in the National Institute of Bioscience and Human-Technology, Advanced Industrial Science and Technology, Agency of Ministry of Economy Trade and Industry, under the deposit number of FERM BP-7477 in terms of Budapest Treaty.

* * * * *